(12) United States Patent
Várkut et al.

(10) Patent No.: US 12,257,009 B2
(45) Date of Patent: Mar. 25, 2025

(54) ARTICULATED ROBOTIC PLATFORM

(71) Applicant: Brainlab AG, Munich (DE)

(72) Inventors: Bálint Várkut, Munich (DE); Dirk Schöttle, Munich (DE)

(73) Assignee: Brainlab AG, Munich (DE)

( * ) Notice: Subject to any disclaimer, the term of this patent is extended or adjusted under 35 U.S.C. 154(b) by 658 days.

(21) Appl. No.: 17/256,713

(22) PCT Filed: Jul. 18, 2019

(86) PCT No.: PCT/EP2019/069413
§ 371 (c)(1),
(2) Date: Dec. 29, 2020

(87) PCT Pub. No.: WO2020/020749
PCT Pub. Date: Jan. 30, 2020

(65) Prior Publication Data
US 2021/0259791 A1    Aug. 26, 2021

(30) Foreign Application Priority Data

Jul. 23, 2018  (WO) ................. PCT/EP2018/069940

(51) Int. Cl.
*A61B 34/30*   (2016.01)
*A61B 34/00*   (2016.01)
(Continued)

(52) U.S. Cl.
CPC ............. *A61B 34/30* (2016.02); *A61B 34/20* (2016.02); *A61B 34/70* (2016.02); *A61B 90/14* (2016.02);
(Continued)

(58) Field of Classification Search
CPC ......... A61B 34/30; A61B 34/20; A61B 34/70; A61B 90/14; A61B 90/57;
(Continued)

(56) References Cited

U.S. PATENT DOCUMENTS

| 2005/0148808 A1 | 7/2005 | Cameron et al. |
| 2007/0120512 A1 | 5/2007 | Albu-Schaffer et al. |

(Continued)

FOREIGN PATENT DOCUMENTS

| WO | 9823216 A1 | 6/1998 |
| WO | 2015/052719 A1 | 4/2015 |

OTHER PUBLICATIONS

International Preliminary Report on Patentability for corresponding International Application No. PCT/EP2019/069413, dated Feb. 4, 2021. 10 Pages.

(Continued)

*Primary Examiner* — Sarah A Long
*Assistant Examiner* — James R McGinnity
(74) *Attorney, Agent, or Firm* — Tucker Ellis LLP

(57) ABSTRACT

An articulated robotic platform is provided as an end-actuator intended to be fitted to an articulated robotic arm. One use of the articulated robotic platform is to more accurately guide surgical tools during a surgical intervention making it possible to achieve positional accuracy on the level of millimeters or fractions of a millimeter. The articulated robotic platform includes support members attached to the patient or anchoring the articulated robotic platform onto a clamp. The support members of the articulated robotic platform are capable of changing in length, and this change can be monitored by an extension measurement sensor fitted to one or more of the support members. The controller, when provided with feedback information of the extension measurement and direction of several of the legs, can calculate accurately the position of the articulated robotic platform relative to an intervention area of a patient.

18 Claims, 6 Drawing Sheets

(51) Int. Cl.
  *A61B 34/20* (2016.01)
  *A61B 90/10* (2016.01)
  *A61B 90/14* (2016.01)
  *A61B 90/57* (2016.01)
  *A61B 90/50* (2016.01)

(52) U.S. Cl.
  CPC ...... *A61B 90/57* (2016.02); *A61B 2034/2055* (2016.02); *A61B 2034/2059* (2016.02); *A61B 2034/2068* (2016.02); *A61B 2034/304* (2016.02); *A61B 2090/103* (2016.02); *A61B 2090/5025* (2016.02)

(58) Field of Classification Search
  CPC .... A61B 2034/2055; A61B 2034/2059; A61B 2034/2068; A61B 2034/304; A61B 2090/103; A61B 2090/5025
  See application file for complete search history.

(56) References Cited

U.S. PATENT DOCUMENTS

| | | | |
|---|---|---|---|
| 2009/0177081 A1 | 7/2009 | Joskowicz et al. | |
| 2011/0319913 A1* | 12/2011 | Labadie | A61N 1/0541 606/130 |
| 2014/0343567 A1 | 11/2014 | Morash | |
| 2016/0192960 A1* | 7/2016 | Bueno | A61B 17/07207 606/110 |
| 2016/0249990 A1* | 9/2016 | Glozman | A61B 34/30 606/130 |
| 2016/0346940 A1 | 12/2016 | Bax et al. | |
| 2016/0367331 A1* | 12/2016 | Nelson | A61B 17/3468 |
| 2017/0014193 A1* | 1/2017 | Ng | A61B 34/20 |
| 2017/0095299 A1* | 4/2017 | Hendrick | A61B 34/30 |
| 2017/0325906 A1* | 11/2017 | Piecuch | A61B 34/25 |
| 2018/0000543 A1* | 1/2018 | Hibner | A61B 34/20 |

OTHER PUBLICATIONS

Kobler et al., "Design and analysis of a head-mounted parallel kinematic device for skull surgery", May 31, 2011, pp. 13.

Chapman et al., "Spine Surgery and the Mazor® Robotics Renaissance Robot: 11 Things to Know", Feb. 28, 2017, 4 pages.

"Hexapod +3 Redundant Measuring Systems / Legs Medical Robot with Highest Levels of Reliability", PI, 1998, 2 pages.

"Cirq Jump-Starting Robotic Assistance", accessed online at https://www.brainlab.com/surgeryproducts/overviewspinaltraumaproducts/cirqrobotics/, May 4, 2018, 4 pages.

"neuromate® robotic system for stereotactic neurosurgery", accessed online at http://www.renishaw.com/en/neuromate-stereotactic-robot-10712, Oct. 4, 2018, 7 pages.

"Rosa Brain", accessed online at https://www.medtech.fr/en/rosa-brain, Oct. 15, 2016, 12 pages.

International Search Report and Written Opinion for corresponding International Application No. PCT/EP2019/069413, dated Sep. 5, 2019. 13 Pages.

Office Action of corresponding European Application No. 19740389.2, dated Oct. 17, 2024, 9 pages.

* cited by examiner a)

b)

ARTICULATED ROBOTIC PLATFORM

RELATED APPLICATION DATA

This application is a national phase application of International Application No. PCT/EP2019/069413 filed Jul. 18, 2019, which claims priority to International Application No. PCT/EP2018/069940, filed on Jul. 23, 2018, the contents of both of which are incorporated herein by reference.

FIELD OF THE INVENTION

The present invention relates to an articulated robotic platform for medical tool positioning, an articulated robotic arm, a system for controlling the position of an articulated robotic platform in proximity to a patient, a computer-implemented method for controlling the position of an articulated robotic platform, a corresponding computer program, and a non-transitory program storage medium storing such a program.

TECHNICAL BACKGROUND

In the field of surgical cranial intervention, there is often a need to place an intervention device inside the cranial cavity of a patient using surgical tools such as electrodes for the purpose of epilepsy treatment, interventions in the regions of the *cochleae*, or the treatment of cancerous objects inside the skull. The accuracy and safety of such procedures is of paramount importance owing to the undesired effects of introducing a surgical tool into the wrong part of a patient's brain. Ideally, sub-millimetre accuracy is desired.

Historically, such surgical cranial interventions were performed using a "head clamp" fixed directly into the bone of a patient's skull. Such head clamps provide a stable reference to a patient that can be used for mounting tool guides and the like during an intervention, and are still widely used. An example of a head clamp (patient support frame) is the "Mayfield frame". More recently, partially automated cranial intervention procedures have been proposed. In particular, fully automated robotic approaches use a large articulated robot to access the target point, whilst the patient's skull is fixed in a head clamp. Another approach involves the mounting (fixation) of a movable platform robotic device directly onto a patient's skull.

However, the articulated robots used in the first method are large and expensive. They are often mounted on a large trolley and are cumbersome in a clinical context. The movable platform robots fixed directly to a patient's skull according to the second approach are unable to target multiple points on a patient's skull quickly and with acceptable precision, and often cannot be used where the trajectory extends over a significant portion of a patient's skull. Furthermore, the skull-fixed robots require the placement of fiducial markers and/or anchor points a significant amount of time in advance of a procedure, often causing the patient discomfort.

Accordingly, improvements to the approaches used in partially automated cranial intervention procedures are still possible. The present invention has the object of improving the approaches applied to partially automated cranial intervention procedures. Aspects of the present invention, examples and exemplary steps and their embodiments are disclosed in the following. Different exemplary features of the invention can be combined in accordance with the invention wherever technically expedient and feasible.

Exemplary Short Description of the Invention

In the following, a short description of the specific features of the present invention is given which shall not be understood to limit the invention only to the features or a combination of the features described in this section.

The articulated robotic platform discussed in this application is generally provided as an end-component intended to be rigidly fitted to the distal end of an articulated robotic arm. One use of the articulated robotic platform is to guide surgical tools more accurately during a surgical intervention on, for example, a patient's skull or spine, making it possible to achieve positional accuracy on the level of millimetres or fractions of a millimetre. The accuracy improvement results from a balance of forces provided between the patient and the articulated robotic arm through the articulated robotic platform.

The combination of an articulated robotic platform having accurate (sub-millimetre) position feedback with an articulated robotic arm having less accurate position feedback enables medical interventions requiring sub-millimetre accuracy to be performed using a relatively inaccurate articulated robotic arm.

The articulated robotic platform comprises support members (legs) attached, for example, to the patient using bone fiducials as landing points (attachment points), although one or more of the support members may optionally anchor the articulated robotic platform onto a "head clamp" or similar. The support members of the articulated robotic platform are capable of changing in length. The position of the articulated robotic platform, in particular the magnitude of the change in length and/or the orientation of the support members can be monitored by a positioning sensor, in particular fitted to one or more support members. The positioning sensor preferably comprises an extension measurement sensor, an orientation sensor like an optical navigation sensor, an angle sensor and/or an x-ray navigation sensor fitted to one or more of the support members. A controller, when provided with feedback data of the position of the articulated robotic platform, comprising the extension measurement and/or the orientation of several (optionally at least three) of the legs, can calculate accurately calculate the position of the articulated robotic platform relative to an intervention area of a patient.

The articulated robotic arm to which the articulated robotic platform is attached functions to provide a counter-balancing force to the articulated robotic platform to hold the articulated robotic platform accurately in a treatment position. In this way, a conventional and optionally inaccurate articulated robotic arm provides coarse-grained positioning functionality (for example, to an accuracy of 1 mm) and a simple and optionally disposable articulated robotic platform provides feedback data that may be used to control the articulated robotic arm (and optionally the articulated robotic platform) to provide fine-grained (sub-millimetre) accuracy. The application discusses several approaches.

The present application considers two main types of articulated robotic platform, although it will be appreciated that variations of both types may be combined. In a passive type, the articulated robotic platform is provided with feedback sensors to communicate, at a minimum the position of the articulated robotic platform to a controller. This type of articulated robotic platform does not have its own force actuators, and relies on a traction force provided by a articulated robotic arm connected to the articulated robotic platform (a force pulling the articulated robotic platform away from an intervention site of a patient). In order to transmit the traction force to the articulated robotic platform, one or more of the support members are optionally lockable (such that their length does not change). Modifications to the vector of the traction force applied by the articulated robotic arm to the passive articulated robotic platform enable accurate positioning and repositioning of the articulated robotic platform over a trajectory entry point, owing to the interaction of the traction force from the articulated robotic arm and the counter-force generated by the anchor points on the patient to which the articulated robotic platform is attached.

Optionally, the passive type of articulated robotic platform is used for measuring distances at an intervention site of the patient. For example, when a passive articulated robotic platform is positioned at intervention site, the movement (e.g. by a medical professional) of support members of the articulated robotic platform into contact with markers on a patient enable the distance between the articulated robotic platform, the intervention site, and the patient to be accurately localised. Preferably, the position sensors of the articulated robotic platform have greater accuracy than position sensors of an articulated robotic arm, so the spatial relationship between the articulated robotic platform and the intervention site can be accurately characterized. In the measurement mode, one or more support members of the articulated robotic platform are free to change in length (i.e. the position of the support members is not locked). A medical professional moves the support members between different anchoring points when the articulated robotic platform needs to move to a new intervention site.

The passive version of the articulated robotic platform may be held in a state of equilibrium relative to an intervention area of the patient when the articulated robotic arm applies a traction force to the articulated robotic platform. A pulling force of the articulated robotic arm equates with an anchoring force exerted on the support members of the articulated robotic platform by the anchoring fiducials.

A second main type of articulated robotic platform considered in the present application, referred to as the active case, provides an active articulated robotic platform resembling the passive type of articulated robotic platform, but also comprising support members having actuators capable of exerting a force on the support members to thus exert a counter-force against the force applied by the articulated robotic arm.

In a first variation of the active case, the articulated robotic arm exerts a traction force pulling the active articulated robotic platform away from the patient, and the active articulated robotic platform exerts a counter-force that attempts to pull the articulated robotic arm towards the anchor points fixed to the patient. Accurate position data of the articulated robotic platform is provided as feedback to a controller to improve the accuracy of the positioning of the articulated robotic platform. Optionally, one or more of the support members is locked so that they cannot change in length. A medical professional moves the support members between different anchoring points when the articulated robotic platform needs to move to a new intervention site.

In a second variation, the articulated robotic arm exerts a pushing force towards the patient, and the actuators of the active articulated robotic platform exert a counter-force as a "pushing" force away from the patient and against the "pushing" force of the articulated robotic arm. Accurate position data of the articulated robotic platform is provided as feedback to a controller to improve the accuracy of the positioning of the articulated robotic platform. Optionally, one or more of the support members is locked so that they cannot change in length. A medical professional moves the support members between different anchoring points when the articulated robotic platform needs to move to a new intervention site.

In a third variation, the support members of the articulated robotic platform comprise actuators offering at least 4 degrees of freedom (4DOF). The actuators can move at least one support member within a substantially hemispherical, or half-hemispherical space around their attachment points, and additionally to lengthen or shorten the support members. Thus, the articulated robotic platform is capable of traversing the anchor points itself based on commands received from a controller, optionally without the assistance of a medical professional.

An articulated robotic platform comprising active actuators may provide additional adjustability against the traction force provided by the articulated robotic arm, and enables the articulated robotic arm to "push" the articulated robotic platform towards the interventional area, with this "pushing" force being balanced by a reaction from the active actuators accommodated on the articulated robotic platform.

The position measurement functionality of the articulated robotic platform enable accurate measurements of the distance between a patient and a robotic arm to be provided, optionally used for registration or surgical guidance purposes.

Furthermore, bone fiducials (landing points) may be provided to enable the articulated robotic platform to move, and/or be moved, along a pre-planned path, such that as the articulated robotic platform successively transfers its support members between the bone fiducials, the entire articulated robotic platform moves between intervention trajectory entry points located on a path over an intervention area of the patient.

A unifying idea is that the accurate positioning sensors of the articulated robotic platform provide feedback data to a controller enabling a more inaccurate articulated robotic arm, to which the articulated robotic platform is attached, to be accurately held in place at an intervention site on a patient (for example, to within sub-millimetre accuracy).

GENERAL DESCRIPTION OF THE INVENTION

In this section, a description of the general features of the present invention is given for example by referring to possible embodiments of the invention. In general, the invention reaches the aforementioned object by providing, according to a first aspect, an articulated robotic platform for medical tool positioning, comprising:

a medical tool support;
a plurality of support members connected to the medical tool support.

The at least one support member comprises an articulated connection to the medical tool support, and a distal end configured to be connectable to an anchor member. The articulated robotic platform comprises a first joint portion configured to secure the articulated robotic platform in a controlled spatial relationship to a robotic arm. The articulated robotic platform further comprises at least one positioning sensor configured for determining a position of the articulated robotic platform.

Advantageously, the articulated robotic platform is capable of moving along an intervention path (for example, over the skull or spinal region of the patient) by successively repositioning (either by a medical professional repositioning the support members, or via native actuators on the articulated robotic platform) its support members. Additionally, a connection to a robotic arm enables the articulated robotic platform to be held in stable equilibrium at millimetre or sub-millimetre accuracy. The stabilisation of the articulated robotic platform afforded by the interaction between the articulated robotic arm and the articulated robotic platform means that automatic control approaches can be used to enable a relatively inaccurate articulated robotic arm and a relatively accurate articulated robotic platform to provide accurate positioning at an intervention site, rather than requiring a robustly constructed and expensive robot, thus relaxing the design requirements of the articulated robotic platform. Thus, the articulated robotic platform may be constructed of a disposable material, for example. Furthermore, the articulated connection between the support members and the medical tool support allows for an unrestricted movement of the distal ends of the support members. Thus, the distal ends of the support members are configured for an unrestricted movement in at least 2 degrees of freedom, preferably 3 degrees of freedom.

The at least one support member is preferably configured so that the position, in particular the length and/or the orientation, of the support member is adjusted actively, for example by an actuator.

According to an exemplary embodiment, the positioning sensor further comprises an optical navigation sensor and/or an x-ray navigation sensor.

Preferably, the optical navigation sensor is configured for determining the position, in particular the length and/or the orientation, of the at least one support member. The position of the support members can be automatically or manually be adjusted in accordance with the determined position of the support members.

Preferably, the x-ray navigation sensor is configured for determining an x-ray image of the patient, in particular the skull of the patient. Dependent on the x-ray image, the position, in particular the length and/or the orientation, of the at least one support member is determined. The position of the support member can automatically or manually be adjusted in accordance with the determined position of the support member.

According to an exemplary embodiment, the at least one positioning sensor is at least partly disposed at the at least one support member.

In other words, parts of the positioning sensor are disposed at the medical tool support and parts of the positioning sensor are disposed at the at least one support member, preferably at the distal end of the at least one support member.

Preferably, optical markers are disposed at the medical tool support as well as at the distal end of the at least one support member. Thus, the length and/or orientation of the at least one support member can be determined dependent on the spatial arrangement of the optical markers to each other. Therefore, only the relative distance of the distal end of the at least one support member to the medical tool support needs to be determined. Preferably, such relative distance lie in a range of about 20 cm. Thus, a camera with a relatively small vision range and thus a relatively high precision can be used to determine the relative distance between the optical markers.

According to an exemplary embodiment, the positioning sensor further comprises an extension measurement sensor configured for measuring an extension of the at least one support member and/or at least one angle sensor configured for measuring an angle between the at least one support member and the medical tool support.

Dependent on the extension of the support member, the position, in particular the length and/or the orientation, of the support member is determined. The position of the support member can automatically or manually be adjusted in accordance with the determined position of the support member.

Dependent on the angle between the at least one support member and the medical tool support, the position, in particular the length and/or the orientation, of the at least one support member is determined. The position of the support member can be automatically or manually be adjusted in accordance with the determined position of the support member.

According to an exemplary embodiment, the extension measurement sensor comprises a tensionable cord fixed to a distal portion of the at least one support member and a cord tensioning reel comprised in a proximal portion of the at least one support member and/or the medical tool support.

Advantageously, by monitoring the extension of support members of the articulated robotic platform, the position of the articulated robotic platform relative to a patient may be calculated. The cord tensioning reel is configured to sense the amount of extension of a support member and to generate extension measurement data for transmission to a controller.

According to an exemplary embodiment, the articulated robotic platform further comprises:
a support hub.

The medical tool support, the plurality of support members, and the joint portion are attached to the support hub.

Advantageously, a support hub may provide further mounting positions for elements of the articulated robotic platform.

According to an exemplary embodiment, the articulated robotic platform further comprises one or more actuators configured to move at least one support member.

Advantageously, the articulated robotic platform can generate its own balancing force (a pulling or pushing force against an articulated robotic platform, for example) to counter balancing force generated by an articulated robotic arm to which the articulated robotic platform is attached furthermore, the provision actuators may enable the articulated robotic platform to automatically move its support members to enable the articulated robotic platform to position itself at the point of an intervention trajectory on a skull, for example, without further human intervention.

According to an exemplary embodiment, the distal end of the at least one support member is configured to be attached to an anchor member provided as a fiducial marker or a patient support frame.

Since the support members are not limited in their extension and/or orientation, the anchor members that will be contacted by the support members can target multiple points on a patient's skull quickly and with an improved precision, and can be used all over a patient's skull. The anchor member preferably comprises a plurality of separate anchor elements. Each of the anchor elements is provided as a fiducial marker. In contrast to an anchor member provided as a single patient support frame, an anchor member with a plurality of independent anchor elements, which can be variably arranged on the patient, each provided as a fiducial marker can take advantage of the flexibility in view of degrees of freedom of the support members. The articulated robotic platform thus is flexible in view of the shape of the patient, in particular the shape of the skull of the patient.

Advantageously, the articulated robotic platform may be securely anchored to a patient during treatment, to enable the generation of balancing forces across the articulated robotic platform in combination with articulated robotic arm.

Preferably, the extension measurement sensor is configured to communicate the linear extension of the at least one support member to a controller and/or a robotic arm via a wireless or a wired communications protocol.

According to an exemplary embodiment, at least one of the articulated robotic platform, a portion of the at least one support member, and the joint portion comprise a radiopaque material, such as a plastic comprising a barium sulphate filler.

Advantageously, before, during, or after an intervention procedure, a imaging scan, for example a CT or X-Ray scan, may be obtained displaying the articulated robotic platform relative to actuators in a CT or X-Ray image. Using appropriate registration techniques, additional position information of the articulated robotic platform may be provided for position control purposes.

According to an exemplary embodiment, the at least one support member comprises an anchor member sensor configured to identify between at least first and second different types of fiducial markers.

Advantageously, different types of fiducial markers may delineate a desired interventional treatment path over the surface of a skull, for example. An articulated robotic platform that is able, via its support members, to identify different types of fiducial markers may be able to report to a controller that it has been placed in an incorrect position by a human operator, for example.

According to a second aspect, an articulated robotic arm for medical tool positioning is provided, comprising:

a plurality of articulated arm sections, wherein a distal articulated arm section of the plurality of articulated arm sections is supported by a base support.

a proximal articulated arm section of the plurality of articulated arm sections comprising a second joint portion configured to secure the proximal articulated arm section to an articulated robotic platform is provided according to the first aspect or its optional embodiments. The robotic arm is configured to apply a balancing force to the articulated robotic platform to thus stabilise the articulated robotic platform.

Advantageously, an articulated robotic arm according to the second aspect is capable, for example, of pulling an articulated robotic platform away from a patient (using an articulated robotic arm to generate a traction force applied to the articulated robotic platform). The articulated robotic arm is able to accurately hold an articulated robotic platform according to the first aspect in a stable equilibrium before, during, and after an intervention on a patient, so that its position with respect to a patient does not change. Accordingly, the position of the patient, the articulated robotic arm, and the articulated robotic platform are registered prior to treatment.

According to a third aspect, a system for controlling the position of an articulated robotic platform in proximity to a patient is provided. The system comprises:

an articulated robotic arm; and an articulated robotic platform according to the first aspect or its embodiments. The first joint portion of the articulated robotic platform is connected to the second joint portion of the robotic arm to enable the articulated robotic platform to balance against a counterbalancing force provided, in operation, by the articulated robotic arm.

According to an exemplary embodiment, the system further comprises:

a controller.

the controller is configured to acquire position configuration data of the articulated robotic arm, position configuration data of the articulated robotic platform, and registration data of the registration between the articulated robotic arm and the articulated robotic platform. The controller is configured to generate control data for at least one of the support members, the articulated robotic arm, and the joint portion of the robotic arm and/or the articulated platform based on the position configuration data of the robotic arm, position configuration data of the articulated robotic platform, and the registration data. The control data is calculated to (i) cause the articulated robotic platform to be held in a stable equilibrium against a counter-force provided by the articulated robotic arm, and (ii) to cause the articulated robotic platform to move relative to an anchor member to which the articulated robotic platform is attached.

According to an exemplary embodiment, the system further comprises:

at least one image or video sensor arranged to obtain an image or a video containing a region of interest, the articulated robotic arm, and the articulated robotic platform. The at least one image or video sensor is configured to acquire an image and/or a video of an anchor member, the articulated robotic platform, and the articulated robotic arm in the region of interest. The controller is configured to generate a mapping of the anchor member to the at least one support member of the articulated robotic platform using the image and/or the video acquired from the at least one image or video sensor.

Advantageously, the provision of image or video data enables the localisation accuracy of the articulated robotic platform relative to the patient and the articulated robotic arm to be further enhanced.

According to a fourth aspect, there is provided a computer-implemented method for controlling the position of an articulated robotic platform according the first aspect or its embodiments in proximity to a patient. The method comprises:

a) acquiring position data of the articulated robotic platform from a positioning sensor of the articulated robotic platform;

b) acquiring position data of an articulated robotic arm supporting the articulated robotic platform;

c) calculating a first balancing force to be applied by the articulated robotic platform to the articulated robotic arm based on the position data of the articulated robotic arm and the position data of the articulated robotic platform;

d) calculating a second balancing force to be applied by the articulated robotic arm to the articulated robotic platform based on the position data of the articulated robotic arm and the position data of the articulated robotic platform;

e) applying the first and second balancing forces to the articulated robotic platform and the articulated robotic arm, respectively, such that the articulated robotic platform is held in a stable equilibrium in relation to the patient.

Optionally, in step b), the articulated robotic arm is an articulated robotic arm according to that described in the second aspect.

According to an exemplary embodiment, applying the first balancing force comprises:
- e1) causing the plurality of support members of the articulated robotic platform to generate a first force in a direction substantially towards a surface of the patient, and
- e2) simultaneously, causing the articulated robotic arm to generate a second force in a direction substantially away from the surface of the patient to counterbalance the first force vector generated by the articulated robotic platform.

According to a fifth aspect of the invention, there is provided a program which, when running on a computer or when loaded onto a computer, causes the computer to perform the method according to any one of the preceding claims;
and/or a program storage medium on which the program is stored;
and/or a computer comprising at least one processor and a memory and/or the program storage medium, wherein the program is running on the computer or loaded into the memory of the computer;
and/or a signal wave or a digital signal wave, carrying information which represents the program;
and/or a data stream which is representative of the program.

In the fifth aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform the method according to the fourth aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore may alternatively or additionally relate to a data stream representative of the aforementioned program.

According to a sixth aspect, there is provided a use of an articulated robotic platform according to the first aspect or its embodiments, and/or an articulated robotic arm according to the second aspect, and/or a system for controlling the position of an articulated robotic platform in proximity to a patient according to the third aspect, for the surgical treatment of a patient.

According to a seventh aspect, the invention is directed to a non-transitory computer-readable program storage medium on which the program according to the fifth aspect is stored.

Definitions

In this section, definitions for specific terminology used in this disclosure are offered which also form part of the present disclosure.

Trajectory

The insertion of an interventional device into a patient follows a trajectory. For example, during electrode stimulation of a brain, an electrode is inserted through a hole in a patient's skull and travels to the treatment region along a trajectory to the treatment location. A trajectory could be followed by a needle, an electrode, or many other surgical interventional devices. In the case of an intervention into the skull, the trajectory is usually a straight line in 3D space beginning at a trajectory entry point typically drilled through the skull, however curved trajectories are also possible.

Path

The term "path" refers to a route that a robotic platform can take between trajectory entry points, ideally with a medical tool support aligned with the path. It will be appreciated that there exist many possible paths between trajectory entry points, which can be calculated as a function of the 3D location of the trajectory entry points, the motion constraints of a robotic platform, and fiducial (attachment anchor) locations on the skull.

Articulated Robotic Platform

An articulated robotic platform in the context of this disclosure is a mechanical article that is mountable on part of a patient's anatomy (for example, the skull or neurocranium, or the spine). In particular, the articulated robotic platform is preferably connectable to fixed support points (fiducial markers) pre-positioned on the patient. The articulated robotic platform is also connectable to an articulated robotic arm using a first joint portion. In use, the articulated robotic arm preferably exerts a stabilising force on the articulated robotic platform. The function of the articulated robotic platform is to provide an accurate and reconfigurable positioning point and support for interventional surgical tools relative to a part of a patient's anatomy, such that the articulated robotic platform can accurately and quickly position and reposition surgical tools along a trajectory inside a part of a patient's anatomy during an intervention.

As discussed in the short summary above, an articulated robotic platform may be of a "passive" type comprising support member position measurement devices, or it may be of an "active" type additionally comprising support member actuators capable of moving the support members of the articulated robotic platform. Optionally, a subset of the support members of the articulated robotic platform may are equipped with actuators.

Large-scale repositioning of the articulated robotic platform occurs by unattaching support members of the articulated robotic platform from a first set of support points and attaching them to a second set of support points at a different position on part of the patient's anatomy. In optional embodiments, repositioning of the articulated robotic platform can also be performed using automatic actuators connected to the support members of the articulated robotic platform.

The repositioning of the automatic robotic platform may be unassisted by a medical professional (for example, using controlled actuation of the support members of the articulated robotic platform and/or robotic arm). The repositioning may be partially or fully assisted by a medical professional. A plurality of support members (legs) are attached to the articulated robotic platform to support it in close proximity to a part of a patient's anatomy. Preferably, the articulated robotic platform comprises a rigid support hub (such as a flat, rigid plastic platform). It will be appreciated that many construction techniques can be applied to create the articulated robotic platform discussed above. For example, the articulated robotic platform may be provided as a rigid injection-moulded, or 3D printed article.

Articulated Robotic Arm

An articulated robotic arm in the context of this disclosure is a mechanical sub-system that may be provided in the region of a surgical intervention area. The articulated robotic arm has a second joint portion capable of connecting to, supporting, and enabling the transmission of forces to the first joint portion of an articulated robotic platform. An exemplary function of the articulated robotic arm is to support an articulated robotic platform as defined in the preceding paragraph in the vicinity of a patient before, during, and after a surgical intervention. A typical robotic arm comprises a plurality of articulated arm sub-sections. An individual articulation of each articulated arm sub-section may be a hinge joint providing 1 degree of freedom (DOF), a ball joint providing three rotational DOF, or any other form of individual articulation. The articulated robotic arm is preferably provided with position control motors and position feedback sensors to enable the accurate positioning of the arm proximal to the patient. Furthermore, the second joint portion provides a mechanical support connection to the first joint of the articulated robotic platform, and optionally may enable the communication of sensor feedback data and/or control data to and from the articulated robotic platform via the first joint portion.

In a "passive" case of an articulated robotic platform, the articulated robotic arm is configured to exert a traction force (pulling force) against the articulated robotic platform to hold the articulated robotic platform in a stable and accurately positioned equilibrium. In an "active" case of an articulated robotic platform the articulated robotic arm is configured to exert either a traction force (pulling force) or a pushing force against the articulated robotic platform to hold the articulated robotic platform in a stable and accurately positioned equilibrium Medical Tool Support A medical tool support in the context of this disclosure is provided as a detachable or integral member of the articulated robotic platform. The function of the medical tool support is to direct a surgical instrument relative to a patient with a high degree of accuracy (preferably sub-mm accuracy). A variety of medical tool supports may be appropriate dependent on the nature of the medical protocol followed. A variety of customised articulated robotic devices having different medical tool supports may be provided for differing medical protocols. For example, a medical tool support may comprise a hollow guide tube normal to the support hub of an articulated robotic platform, and penetrating through the support hub. A hollow guide tube would enable a treatment electrode to be fed into a pre-drilled hole at a trajectory entry point of a intervention region of the patient, for example. The relative position, in particular extension, of the support members defines the inclination of a medical tool when inserted into the articulated robotic platform, and thus the approach angle of the medical tool (such as an electrode). Optionally, the medical tool supports may be detachable (interchangeable) from the articulated robotic platform. Optionally, a support hub of the articulated robotic platform and the medical tool support may be integrally formed, for example by an injection moulding process or by 3D printing.

Support Member

Support members of the articulated robotic platform function to transmit force between an anchor member fixed to a part of a patient's anatomy to the articulated robotic platform, and eventually to an articulated robotic arm holding the articulated robotic platform. A proximal end of each support member optionally attaches the support member in an articulated relationship to the articulated robotic platform. A distal end of each support member is attachable to, for example, a support element provided on the patient such as a fiducial marker. The support members are configurable into a range of lengths using, for example, a telescoping mechanism. As such, the support members can optionally be implemented as a plurality of concentric telescopic tubular members in a slidable relationship. Other variations, such as the provision of sliding planar support members may also be used. In particular, the support members may optionally be provided with articulated connections also at the distal end, or at intermediate points along the support member to enable the articulated robotic platform to be positioned with more degrees of freedom. Measuring the length of each support member of the plurality of support members together enables the localisation of an articulated robotic platform relative to an interventional area of the patient (in other words, enables position feedback of the articulated robotic platform to be provided to a control system). In an "active" case of the articulated robotic platform, a subset or all of the support members are movable using actuators.

Articulated Connection

Support members of the articulated robotic platform have an articulated connection (kinematic joint) to the medical tool support. Many general types of articulated joint may be used alone or in combination such as a prismatic joint, revolute joint, helical joint, cylindrical joint, spherical joint, planar joint, or combinations of these. The function of the articulated connections is firstly to accurately hold the articulated robotic platform in a stable spatial relationship at an intervention point of a patient's body (for example, on the patient's skull or spine). Secondly, the articulated connections function to enable a position reconfiguration of the articulated robotic platform relative to an intervention point of a patient's body (for example, to allow an interventional path over a patient's skull to be provided). Any mechanical sub-assembly enabling the performance of these functions can be used as articulated connection of the articulated robotic platform. Relative to the articulated robotic platform, an articulated connection is defined to enable movement of a support member through the azimuth plane, the inclination plane, or optionally both planes of the articulated robotic platform. For the purposes of this disclosure, the azimuth plane relative to the articulated robotic platform is coplanar with the support hub of the articulated robotic platform (for example, if the support hub of the articulated robotic platform is a rigid polycarbonate sheet, the azimuth plane is coplanar with the rigid polycarbonate sheet). In colloquial terms, movement of the support member in the azimuth plane resembles a "backward and forwards" movement of a spider's leg. For the purposes of this disclosure, the inclination plane relative to the articulated robotic platform is normal to the azimuth plane. In colloquial terms, movement of the support member in the inclination plane resembles an "up and down" movement of a spider's leg. It will be appreciated that it is not essential for the articulated connection to be capable of movement in both the inclination and the azimuth planes, although this provides the most versatile articulated connection. For example, the articulated connection may be a "hinge" only connection enabling movement of the support member in the inclination plane.

It will furthermore be allowed that it is not essential that all articulated connections of the articulated robotic platform are identical or of the same type. In the plurality of support members of the articulated robotic platform, a variety of types of articulated connection may be provided. For example, a first and a second support member may be connected to the articulated robotic platform using a "ball-and-socket" joint, whereas third and fourth support members may be connected to the articulated robotic platform using a "hinge" connection.

Optionally, a proximal end of a support member is attached to the articulated robotic platform using a hinge joint having one DOF. Optionally, a proximal end of a support member is attached to the articulated robotic platform using a ball joint having three DOF.

Joint Portion

The articulated robotic platform and the articulated robotic arm are connected by a joint portion. A first joint portion is provided as part of the articulated robotic platform. A second joint portion is provided as part of the articulated robotic arm, preferably the distal end of the articulated robotic arm furthest away from the base of the articulated robotic arm. The first joint portion and the second joint portion may be brought into a fixed and interlocking spatial relationship together forming the joint portion. The function of the joint portion is to hold the articulated robotic platform in a fixed spatial relationship with the articulated robotic arm. Another function of the joint portion is to enable the mutual transmission of forces between the articulated robotic platform and the articulated robotic arm, so that the articulated robotic platform can be held in a state of equilibrium at the intervention region and/or a trajectory point on the patient's skull or spine, for example. Optionally, the joint portion may facilitate the communication of data between the articulated robotic platform and the articulated robotic arm (ultimately to a controller). Optionally, data communicated from the articulated robotic platform to the articulated robotic arm and controller may comprise data about the position, in particular extension, (leg) of each support member of the plurality of support members, inclination data of the articulated robotic platform obtained from a MEMS accelerometer, identification data of a fiducial marker attached to each of the plurality of support members, and data useful for generating a control response for an articulated robotic platform, for example. Optionally, data communicated from the articulated robotic arm to the articulated robotic platform may comprise control signals of optional actuators for moving the plurality of support members in their individual azimuth and inclination plains, or control signals for optional actuators for extending or retracting each of the plurality of support members. Optionally, the data may be communicated using a wired data connection, or a short-range wireless connection.

Controlled Spatial Relationship

The articulated robotic platform may be stabilised using the first joint portion when connected to a second joint portion of the articulated robotic arm in a controlled spatial relationship. The function of the controlled spatial relationship is to balance a force vector applied by the articulated robotic arm to the articulated robotic platform to the force vector applied by the articulated robotic platform to the articulated robotic arm such that the articulated robotic platform is held in a stable equilibrium at the desired intervention site of the patient (for example, on the patient's skull or spine). This enables positioning of the articulated robotic platform to millimetre or sub-millimetre accuracy during a medical intervention, even though the articulated robotic platform is lightweight. A controller may receive a variety of feedback signals from the articulated robotic platform and the articulated robotic arm, and transmit a variety of control signals to the articulated robotic platform and the articulated robotic arm. As one example, a state-space controller, a proportional integral derivative (PID) controller, or a Kalman filter executed in a controller may be configured to receive data transmitted from the articulated robotic platform and the articulated robotic arm, and to generate feedback signals to the articulated robotic platform and the articulated robotic arm based upon the criterion that the articulated robotic platform and the articulated robotic arm should be held in a stable equilibrium during the treatment phase of intervention. Optionally, an artificial intelligence and/or machine-learning algorithm could be pre-trained to perform this control function.

Actuator

Optionally, the articulated robotic platform is provided with one or more actuators configured to move the plurality of support members. The actuators may, for example, be a micro-stepping motor, a "rack and pinion" arrangement connected to a support member, a linear motor, or the like. A first function of the actuators is to move each support member of the plurality of support members through the inclination and azimuth planes to enable the articulated robotic platform to move along a path to, and be held at, an intervention site of a patient by moving the support members between a variety of pre-placed fiducial markers, for example. A second function of the actuators is to provide the articulated robotic platform's component of the balancing force to be exerted against the articulated robotic arm to enable the articulated robotic platform to be held in a stable equilibrium at the intervention site of the patient. Another set of actuators may function to change the length of each support member of the plurality of support members where these are provided with a telescoping (length-changing) function. Of course, independent actuators may be provided to perform these functions independently, or the same actuators may fulfil two or more of these functions. Optionally, the first joint portion may comprise an actuator configured to exert a component of the balancing force between the articulated robotic platform and the articulated robotic arm.

Extension Measurement Sensor

The plurality of support members of the articulated robotic platform are each provided with an extension measurement sensor. This enables an assessment of the length of each support member to be obtained and provided to a controller. In a mode where the articulated robotic platform is passive (in other words, it does not contain any native actuators, and the articulated robotic platform is held in equilibrium exclusively by a traction force applied by the articulated robotic arm), the length data of the extension of each support member can be used to derive position feedback of the articulated robotic platform. In a case where an articulated robotic platform is provided having actuators to control the inclination, azimuth, and extension of the support members, the extension measurement sensors provide extension data of the legs which may be used to control the feedback applied to the inclination, azimuth, and extension actuators of the support members. In practical terms, an example implementation of an extension measurement sensor is to use a sprung drum configured to deploy a thin tensioning wire to the end of a support member. As the support member extends in length, the wire also extends in length as it is deployed from the drum. As the support member reduces in length, the spring in the drum causes the drum to collect the tensioning wire. A number of revolutions or partial revolutions of the drum clockwise and anticlockwise may be tracked using, for example, a rotary encoder, and having knowledge of the circumference of the drum is possible to calculate the extension of the support member of the articulated robotic platform accurately (to within fractions of a millimetre). Optionally, the extension measurement sensor may be provided as a linear encoder arrangement reading a linear encoding scale from the support member as it is extended and retracted.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Registering

The n-dimensional image of a body is registered when the spatial location of each point of an actual object within a space, for example a body part in an operating theatre, is assigned an image data point of an image (CT, MR, etc.) stored in a navigation system.

Image Registration

Image registration is the process of transforming different sets of data into one coordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Marker

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Imaging Geometry

The information on the imaging geometry preferably comprises information which allows the analysis image (x-ray image) to be calculated, given a known relative position between the imaging geometry analysis apparatus and the analysis object (anatomical body part) to be analysed by x-ray radiation, if the analysis object which is to be analysed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the centre of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to an image plane (for example, the plane of an x-ray detector). With respect to the connection between three-dimensional analysis objects and two-dimensional analysis images as defined by the imaging geometry, reference is made for example to the following publications:
1. "An Efficient and Accurate Camera Calibration Technique for 3D Machine Vision", Roger Y. Tsai, Proceedings of the IEEE Conference on Computer Vision and Pattern Recognition. Miami Beach, Florida, 1986, pages 364-374
2. "A Versatile Camera Calibration Technique for High-Accuracy 3D Machine Vision Metrology Using Off-the-Shelf TV Cameras and Lenses", Roger Y. Tsai, IEEE Journal of Robotics and Automation, Volume RA-3, No. 4, August 1987, pages 323-344.
3. "Fluoroscopic X-ray Image Processing and Registration for Computer-Aided Orthopedic Surgery", Ziv Yaniv
4. EP 08 156 293.6
5. U.S. 61/054,187

Referencing

Determining the position is referred to as referencing if it implies informing a navigation system of said position in a reference system of the navigation system.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT).

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Fixed (Relative) Position

A fixed position, which is also referred to as fixed relative position, in this document means that two objects which are in a fixed position have a relative position which does not change unless this change is explicitly and intentionally initiated. A fixed position is in particular given if a force or torque above a predetermined threshold has to be applied in order to change the position. This threshold might be 10 N or 10 Nm. In particular, the position of a sensor device remains fixed relative to a target while the target is registered or two targets are moved relative to each other. A fixed position can for example be achieved by rigidly attaching one object to another. The spatial location, which is a part of the position, can in particular be described just by a distance (between two objects) or just by the direction of a vector (which links two objects). The alignment, which is another part of the position, can in particular be described by just the relative angle of orientation (between the two objects).

Medical Workflow

A medical workflow comprises a plurality of workflow steps performed during a medical treatment and/or a medical diagnosis. The workflow steps are typically, but not necessarily performed in a predetermined order. Each workflow step for example means a particular task, which might be a single action or a set of actions. Examples of workflow steps are capturing a medical image, positioning a patient, attaching a marker, performing a resection, moving a joint, placing an implant and the like.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein FIG. 1a) illustrates a schematic plan view of an example of an articulated robotic platform according to the first aspect.

DESCRIPTION OF EMBODIMENTS

Figure 1:
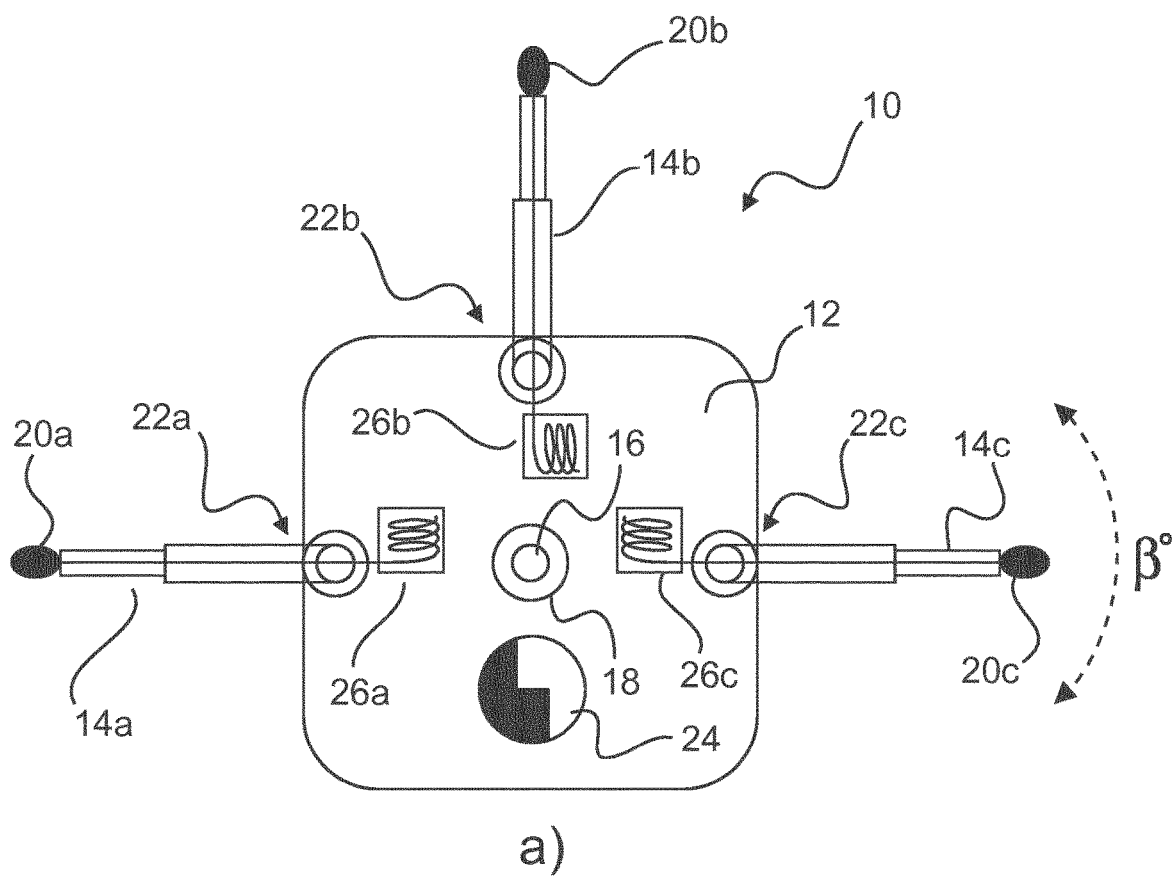
FIG. 1b) illustrates a schematic side view of the example of an articulated robotic platform according to the first aspect as also shown in FIG. 1a).
Figure 1:
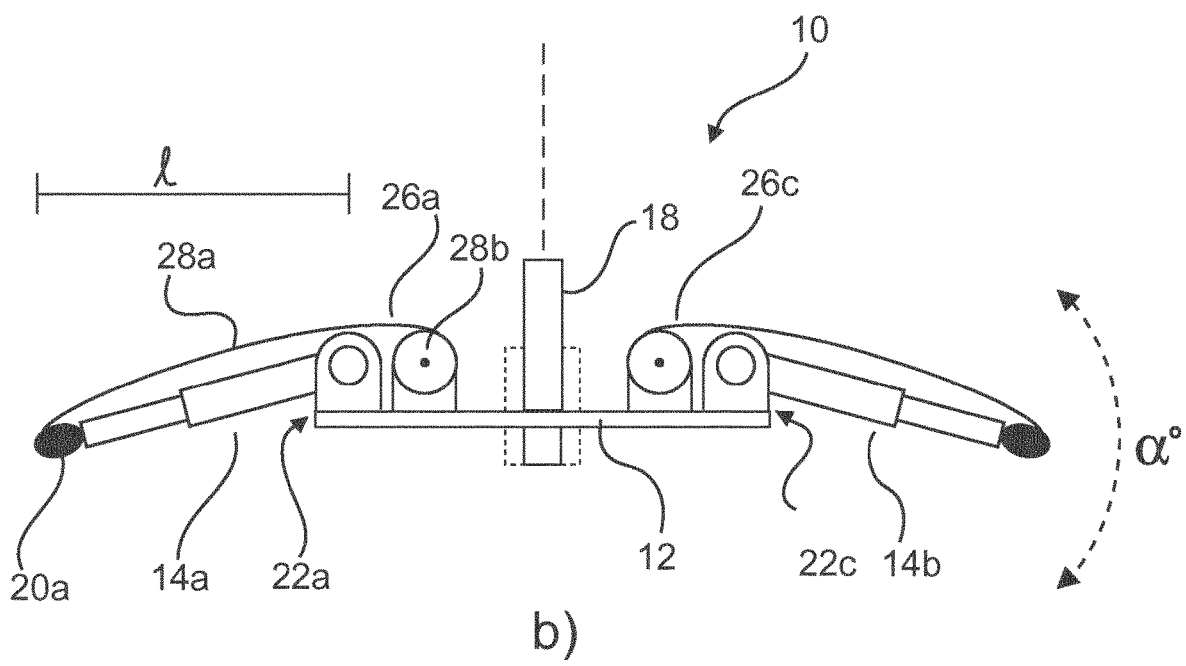

A passive version of an articulated robotic platform will firstly be described, although it will be appreciated that these elements are also incorporated as part of an active articulated robotic platform.

In the presented embodiments, the position sensor of the articulated robotic platform comprises an extension measurement sensor. However, the position sensor is not limited to such an embodiment. Moreover, the position sensor can also be an optical navigation sensor, an angle sensor disposed at the at least one support member and/or an x-ray navigation sensor.

FIG. 1a) illustrates a schematic plan view of an example of an articulated robotic platform 10. It comprises a base member 12 functioning to support a plurality of support members 14a, 14b, 14c. The base member 12 may, for example, be fabricated from a rigid polycarbonate sheet and optionally have a radiopaque property (for example, using barium sulphide impregnated plastic), although many other materials may be used.

An aperture 16 is provided through the centre of the base member 12 (although the aperture could be at any other position of the base member 12). A medical tool support 18 is (integrally or removably) provided through the aperture 16. For example, the medical tool support 18 may be an integral portion of the polycarbonate base member 12. Alternatively, the medical tool support 18 is provided in a threaded or "interference fit" relationship with the base member 12. The medical tool support 18 functions to allow a medical professional to accurately guide a surgical instrument along an intervention path during treatment of a patient. The path passes through one or more trajectory entry points into a patient's skull. For example, the medical tool support 18 can provide support for an electrotherapy electrode to be positioned in a position within the skull when treating epilepsy patients. It will be appreciated that medical tool supports 18 of many different forms can be provided (for example, drill guides, electrode guides) to enable medical tools to be accurately positioned during treatment.

A spatial relationship between medical tool support 18 and the intervention region of a patient is defined by the distance and inclination of the base member 12 from the intervention region of the patient. Accordingly, a plurality of support members 14a, 14b, 14c are attached to the base member 12 (in the illustrated case, three, although the skilled person will appreciate that two or four, five, six, seven, eight, or greater than eight support members may be provided).

A first joint portion 24 fixed to the base member 12 enables the articulated robotic platform 10 to be rigidly attached to a motion effector such as an articulated robotic arm 32. The fact that the first joint portion 24 is rigid means that a force applied to the first joint portion 24 of the articulated robotic platform 10 by an articulated robotic arm (not shown in FIG. 1a) and b)) will be directly transmitted to the articulated robotic platform 10. The first joint portion 24 is optionally formed to have an improved torque handling capability. For example, the first joint portion 24 is provided as a polycarbonate cylinder with a crenelated outer pattern to match a crenelated outer pattern of a second joint portion on a distal end of an articulated robotic arm to which the articulated robotic platform 10 can be attached. Optionally, the joint portion 24 may carry an electrical connector to carry data communications between the articulated robotic platform 10 and a controller via an articulated robotic arm.

In the exemplary articulated robotic platform 10 illustrated in FIGS. 1a) and 1b), the distal ends of each of the plurality of support members are provided with distal ends 20a, 20b, and 20c configured to be connectable to a plurality of anchor members (for example, fiducials). For example, the anchor members are fiducials anchored in a patient's skull prior to the beginning of interventional treatment.

In the illustrated example, the articulated robotic platform 10 comprises support members 14a, 14b, 14c that are attached to the base member 12 at the proximal ends of the support members by articulated connections 22a, 22b, 22c.

The articulated connections 22a, 22b, 22c are, for example, provided as one of the general types of articulated joint alone or in combination such as a prismatic joint, a revolute joint, a helical joint, a cylindrical joint, a spherical joint, a planar joint, or combinations of these. In case of a prismatic joint (the hinge) the support member can move with one degree of freedom (yaw or pitch) (DOF), whereas a more conjugated joint such as a spherical joint enables the support member to move with two DOF (yaw and pitch).

Optionally, the articulated connections comprise orientation sensors (not illustrated) configured to collect orientation angle data of one or more of the support members 14a, 14b, 14c and to provide the orientation angle data as feedback to a controller.

The support members 14a, 14b, and 14c illustrated in FIGS. 1a) and 1b) are configured to have a variable length (extension). The telescoping action provides a further degree of freedom to the support members 14a, 14b, and 14c.

Optionally, in a passive version of the articulated robotic platform 10 with no powered actuators configured to measure distances at the intervention site, the support members 14a, 14b, and 14c change their length using, for example, a telescoping mechanism as the articulated robotic platform 10 is pulled in three-dimensions by an articulated robotic arm, or as a medical professional repositions the support members 14a, 14b, and 14c. In the illustrated example, they comprise two concentrically arranged telescopic members in slidable relationship capable of changing their total length of extension l, however many other mechanisms enabling a variable-length support member could be used.

The exemplary articulated robotic platform 10 illustrated in FIGS. 1a) and 1b) comprises spherical joints as articulated connections 22a, 22b, 22c enabling each of the telescopic support members 14a, 14b, and 14c to move with three DOF. Accordingly, each support member 14a, 14b, and 14c can move along an arc β degrees in an azimuth plane (coplanar with the base member 12) and along an arc α degrees in an inclination plane (normal to the azimuth plane).

However, it will be appreciated that different articulated connections 22a, 22b, 22c may be provided with different types of joint. Indeed, one or more support members can be provided without any articulated connection. Furthermore, although in FIGS. 1a) and 1b) the support members are illustrated having articulated connections 22a, 22b, 22c at proximal ends of the support members relative to the base member 12, this is not essential and indeed the support members may optionally be rigidly fixed to the base member 12, with an articulated connection being provided mid-way, or a proportion of the support member away along the support members 14a, 14b, and 14c.

The illustrated exemplary embodiment of the articulated robotic platform comprises extension measurement sensors 26a, 26b, 26c enabling the feedback of support member linear extension data to a controller (optionally via an electrical data connection through the first joint portion 24, or optionally via a short-range wireless data connection). In the example of FIG. 1, the linear extension of each support member is measured using a taut measurement cord 28a wrapped around a sprung drum 28b. With this type of linear extension measurement sensor, a support member 14a in its shortest (retracted) position implies that the measurement cord 28a will be fully wrapped around the sprung drum 28b (excepting the length of measurement cord required to pass from the sprung drum 28 to the end of the retracted support member 14a). When an articulated robotic arm applies a traction force to the articulated robotic platform, for example, the movement of base member 12 causes a telescopic lengthening of support member 14a in response. The measurement cord 28a is thus progressively deployed from the sprung drum 28b. As a support member shortens, the sprung drum collects the measurement cord 28b. The sprung drum 28b may comprise, for example, a rotary encoder enabling the generation of extension measurement data of the support member 14a during his extension. The extension measurement data 14a may be transmitted via an electrical connection in the first joint portion (or via a short-range wireless network) to a controller.

It will be appreciated that the illustrated and described example of an extension measurement sensor based upon a sprung drum 28b holding a taut cord 28a is one example, and alternatively the support members 14a, 14b, 14c of the articulated robotic platform 10 are provided with linear encoders or other extension measurement devices.

In a variation, the distal ends 20a, 20b, 20c of the support members 14a, 14b, and 14c are provided with distal ends configured to be capable of detecting the identity of an anchor member that they are attached to, or are about to be attached to, and are furthermore capable of transmitting this information to a controller via the first joint portion 24 or a short-range wireless connection. The identity of an anchor member may be detected, for example, by using anchor members having RFID tags, and by providing RFID readers on the distal ends 20a, 20b, 20c of the support members 14a, 14b, and 14c. Accordingly, the articulated robotic platform is capable of detecting additional position information provided by the RFID-enabled fiducial markers have a known position on a interventional region of a patient, in combination with surgical plan data.

Optionally, one or more of the distal ends 20a, 20b, 20c may be attached to a set of fiducial markers using, for example, a screw connection or a "snap connection" using high-strength magnets (such as neodymium magnets).

Thus, the above-described "passive" articulated robotic platform can measure its spatial relationship to the intervention site using accurate extension measurement sensors.

An "active" version of the articulated robotic platform 10 will now be discussed. The active version is common to the "passive version" discussed above but additionally comprises actuators (not illustrated) connected to the support members 14a, 14b, 14c and configured to exert a force on the support members. The actuators are configured to change the length of the support members 14a, 14b, 14c, or optionally a subset of the support members. Preferably the actuators are configured to control the length of the support members 14a, 14b, 14c to within sub-millimetre accuracy.

Optionally, the actuators of the support members 14a, 14b, 14c are supplemented with a locking actuator, or have a locking function, to stiffen the support members 14a, 14b, 14c such that they do not change in length when force are applied from their distal or proximal ends. Accordingly, the articulated robotic platform 10 is positioned in a treatment position, and one or more of the support members 14a, 14b, 14c

Optionally, the articulated robotic platform 10 as illustrated in FIGS. 1a) and 1b) may be provided with actuators enabling a lengthening or shortening force to be applied to the support members 14a, 14b, 14c. For example, in FIG. 1a), the drums of extension measurement sensors 26a, 26b, and 26c are optionally provided as servomotors enabling a pulling force to be applied to the cords 28a, 28b, 28c, which in turn acts to shorten the support members 14a, 14b, 14c in the absence of a connection of the support members 14a, 14b, 14c to an anchor point. When the support members 14a, 14b, 14c are attached to anchor points, the pulling force thus applied functions to pull the articulated robotic platform towards the intervention site. By applying different degrees of tension applied to each of the cords 28a, 28b, 28c enable the force vector pulling the articulated robotic platform 10 to be finely controlled. Extension measurement data of one or more support members 14a, 14b, 14c, and optionally force feedback data of one or more support members 14a, 14b, 14c can be provided to a controller. When the articulated robotic platform 10 is attached to an articulated robotic arm 32 providing an opposite force (attempting simultaneously to pull the articulated robotic platform 10 away from the intervention site), a force balance may be generated enabling the articulated robotic platform to be held in a fine force balance at sub-millimeter accuracy.

Optionally, one or more of the support members 14a, 14b, 14c of the articulated robotic platform 10 is provided with actuators capable of extending the support members 14a, 14b, 14c—in other words, capable of exerting a pushing force away from an intervention site of a patient. For example, the one or more actuators are provided as a rack and pinion capable of exerting an extending and a retracting force on the support members 14a, 14b, 14c.

Accordingly, the articulated robotic platform 10 can, in use, push itself away from the intervention site of the patient. Of course, in this case the articulated robotic arm 32 balances the force of the articulated robotic platform 10 by pushing down against it towards the intervention site, rather than providing a traction force as discussed above.

Optionally, one or more of the support members 14a, 14b, 14c of the articulated robotic platform 10 is provided with actuators capable of extending or retracting the support members 14a, 14b, 14c—in other words, capable of exerting a pushing or a pulling force away from an intervention site of a patient. For example, the one or more actuators are provided as a rack and pinion capable of exerting an extending and a retracting force on the support members 14a, 14b, 14c.

In this case, the controller is configured to cause a first actuator to apply an extending force to a first support member 14a, and a retracting force to a second support member 14b. This enables the articulated robotic platform 10 to provide more complicated for vectors as a counterforce to the articulated robotic arm.

Figure 2A:
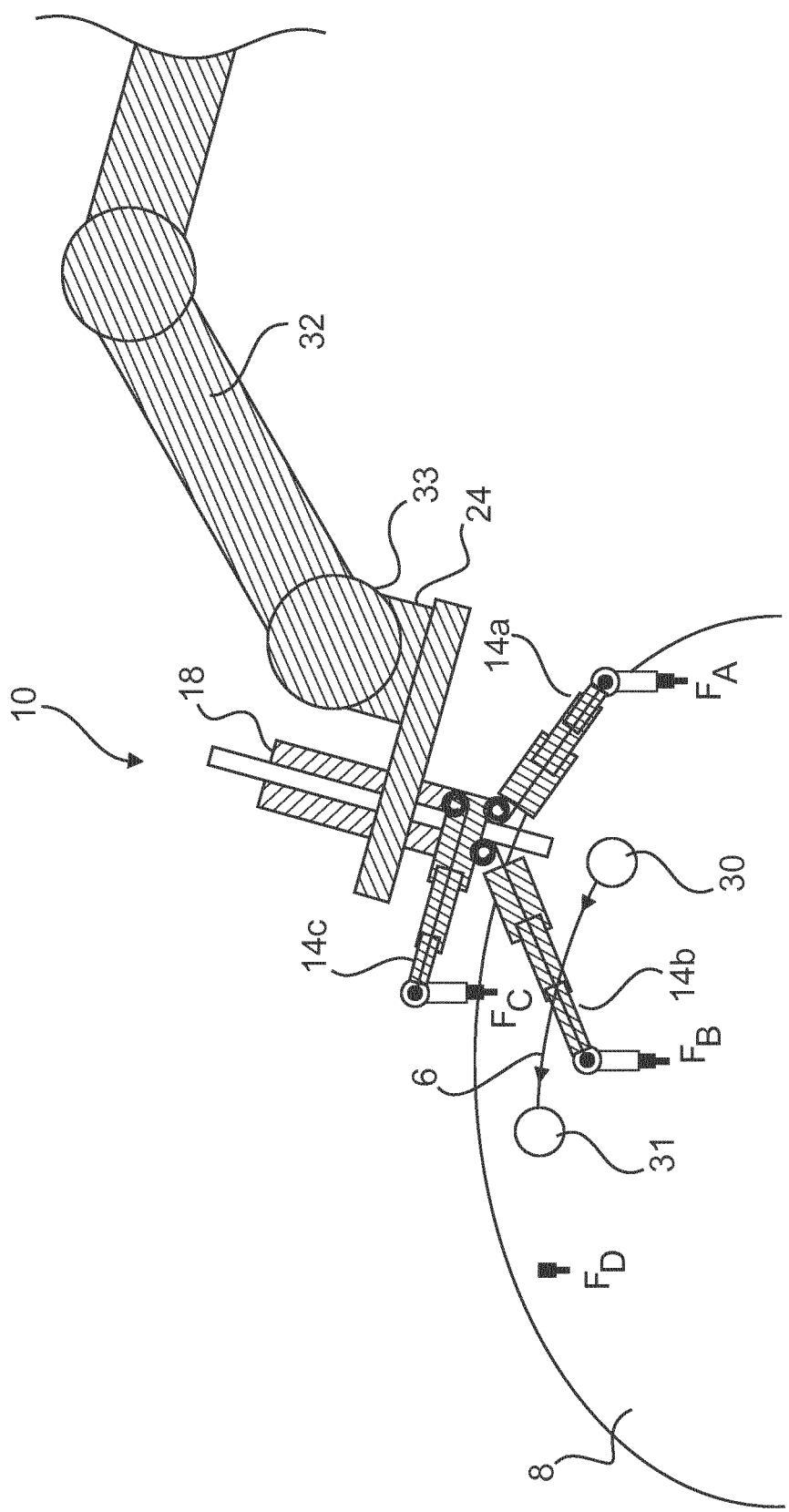
FIG. 2a) schematically illustrates an example of an articulated robotic platform in use at a first trajectory entry location.

FIGS. 2a) and 2b) illustrates the articulated robotic platform 10 in use during an intervention.

As shown in FIG. 2a), in use, an intervention may need to be made, for example, along path 6 on a patient's skull (cranium) 8. The patient's skull comprises fiducial markers $F_A$, $F_B$, $F_C$, and $F_D$ which have been pre-positioned (anchored into the bone of the skull) along a path 6 to enable the articulated robotic platform 10 to be located at desired trajectory entry points. Features 30 and 31 schematically represent two trajectory entry points on a patient's skull (in other words, the point at which an interventional tool can enter a hole that has been pre-drilled into the skull.

In use, the articulated robotic platform 10, a robotic arm is rigidly attached (for example, by medical professional) to an articulated robotic arm 32 via its first joint portion 24. The distal ends of support members 14a, 14b, and 14c are attached (for example, by medical professional) to the skull of the patient 8 via the fiducial anchor points $F_A$, $F_B$, $F_C$ attached to support members 14a, 14b, and 14c, respectively. The articulated robotic platform 10 receives extension measurement data from extension sensors 26a, 26b, 26c and transmits the extension measurement data via the first joint portion 24a and the robotic arm 32 to a controller (not shown). From the three items of extension measurement data, and a registered representation of the patient's anatomy relative to the articulated robotic arm, the controller can calculate the position and inclination of the articulated robotic platform 10 relative to the patient. The articulated robotic arm 32 controller generates position commands for the articulated robotic arm 32 that cause the articulated robotic platform 10 to be held in state of stable equilibrium, with a traction (pulling) force applied by the articulated robotic arm 32 to the patient through the articulated robotic platform 10 balanced by an equal and opposite reaction to the pulling force of the articulated robotic arm 32 provided by a pulling force towards the intervention site of the patient generated by the actuators of the support members 14a, 14b, 14c transmitted as the sum of forces from the fiducial anchors $F_A$, $F_B$, $F_C$ to the robotic arm.

A medical professional is then able to perform an intervention at a trajectory entry location with millimetre or sub-millimetre accuracy, for example positioning a surgical tool into a first trajectory entry point 30 on the path 6 via the medical tool support 18.

Figure 2B:
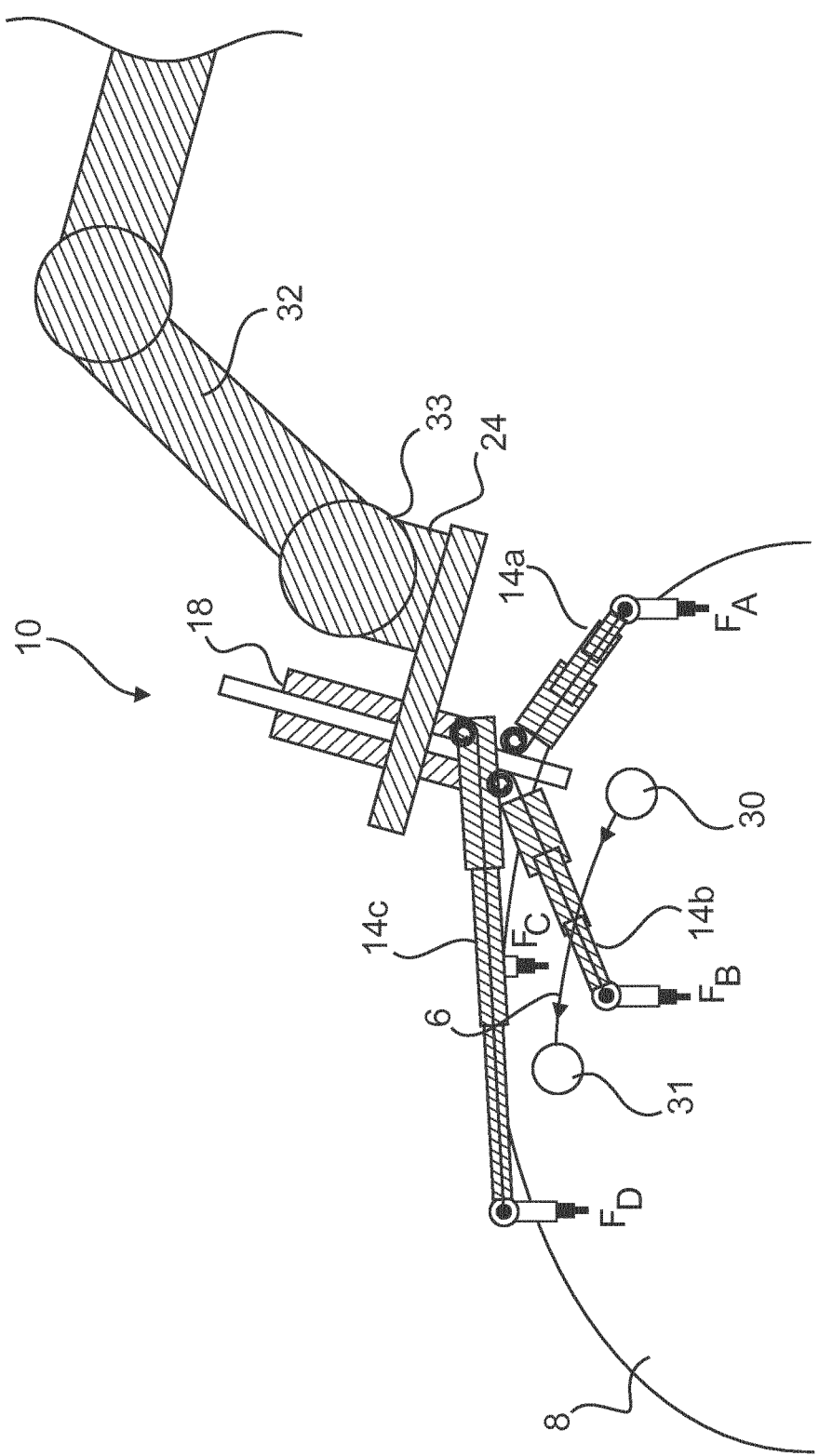
FIG. 2b) schematically illustrates an example of an articulated robotic platform during a transition between first and second trajectory entry locations.
Figure 2C:
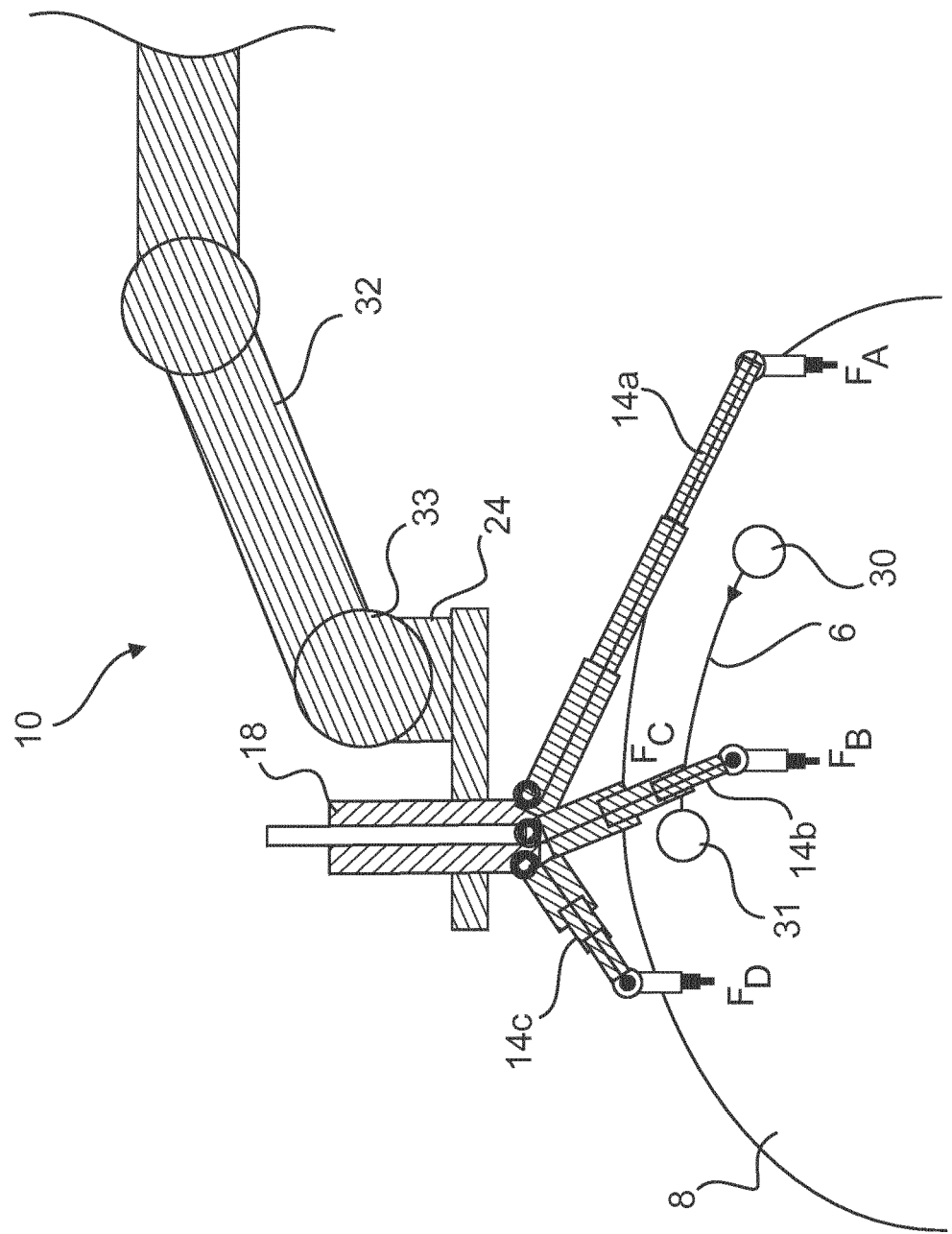
FIG. 2c) schematically illustrates an example of the articulated robotic platform of FIG. 2a) having been moved along an interventional path on a skull to a second trajectory entry location.

At the completion of the first stage of the intervention, there is a need to move the articulated robotic platform 10 from its first position into a subsequent position on the interventional path 6. Turning to FIG. 2b), support element 14c is therefore detached from fiducial $F_C$, and reattached to fiducial $F_D$, as allowed by extension of support member 14c. This action may be performed entirely by a medical professional. The updated position of the articulated robotic platform is shown at FIG. 2c), with the platform having changed position to enable the insertion of a medical tool into a second trajectory entry location 31.

The articulated robotic arm 32 is instructed to move as the articulated robotic platform 10 is moved to its new position, and is configured to cooperate and move with the articulated robotic platform 10. When the support member 14c is attached to the fiducial $F_D$, the articulated robotic arm 32 detects extension data of the support elements 14a, 14b, 14c and repositions itself to ensure that the centre of the medical tool support 18 is stabilised in position over the next desired trajectory entry point of the interventional path 6. A medical professional then performs the next act of interventional protocol. It will be appreciated that more complicated trajectories can be defined provided an acceptable number of fiducial markers is provided.

In the "passive case" of the articulated robotic platform 10, force generation is from the articulated robotic arm 32 via the mechanism of "traction". In other words, the articulated robotic arm 32 pulls the articulated robotic platform 10 away from the patient 8. Feedback data from the extension measurement sensors on the articulated robotic platform 10 enables the articulated robotic arm 32 to generate the equilibrium which enables the sub-millimetre accuracy.

It is not essential that extension measurement data is transmitted from the articulated robotic platform to an external controller. For example, in an optional embodiment the articulated robotic platform 10 and the articulated robotic arm 32 could operate according to a "distributed computing" paradigm in which the articulated robotic platform 10 itself comprises a processing element such as a microprocessor (not shown) configured to receive the extension measurement data from the extension sensors 26a, 26b, 26c and to transmit the required force data to the articulated robotic platform 10.

The articulated robotic platform 10 optionally comprises a force sensor (such as a load cell strain gauge) to measure the force applied to the articulated robotic platform 10 at the first joint portion 24. The processor on the articulated robotic platform then calculates a required force demand to be applied by the articulated robotic arm 32 and communicate the force demand to the articulated robotic arm 32 via the first joint portion 24, to enable the articulated robotic platform 10 to be held in a stable equilibrium.

Accordingly, a design of an end-actuator (articulated robotic platform 10) using bone fiducials as "landing points" is provided. This combines the benefits of skull-mounted robotic approaches with the benefits of conventional robotic arm systems, whilst being flexible enough that multiple trajectories can be executed by using the spider-like articulated robotic platform 10 to occupy different positions between bone fiducial fixation points.

Because the articulated robotic platform 10 as described can be quickly adjusted, the fiducials can be placed and used just in time for the surgery. Additionally, they can also serve as highly accurate registration points for the actual navigation registration between the patient 8, the articulated robotic platform 10 and the articulated robotic arm 32.

This approach combines increased accuracy via the combination of skull-mounted fixation and robotic positioning to reach higher accuracy for neurosurgical implementation (for example) or biopsy procedures. In addition, because the fiducials are placed just before and removed directly after surgery, less stress is caused to the patient making a displacement of the fiducials less likely to happen.

The articulated robotic platform 10 is held in a stable equilibrium owing to balanced forces resulting from the traction of the articulated robotic arm 32 and a reaction force from the patient fiducials. Accordingly the articulated robotic platform 10 may be made of a lighter material than conventional solutions. For example, the parts of the articulated robotic platform 10 may be implemented using polycarbonate plastic, rigid carbon fibre materials, or 3D printed plastic. Accordingly, the total weight of the articulated robotic platform 10 is in the range of 25 grams to 250 grams, 25 grams to 200 grams, 25 grams to 150 grams, 25 grams to 125 grams, 25 grams to 100 grams, or 25 grams to 75 grams.

Optionally, one or more of the distal ends of the support elements 14a, 14b, 14c may be configured to attach to a landing point on a conventional head clamp, further enhancing the positional accuracy of the articulated robotic platform 10 whilst still enabling a interventional path 6 to be followed along the remaining fiducial markers.

When the articulated robotic platform 10 is held against anchoring points on a patient, and an articulated robotic arm 32, the actuators are configured to exert a counterbalancing force against the articulated robotic arm 32 and the anchor points. If the articulated robotic arm 32 exerts a traction force against the articulated robotic platform 10, then the actuators will exert a "pushing force" against the articulated robotic arm 32 as a counterbalancing force. If the articulated robotic arm 32 exerts a "pushing" force towards the intervention site of the patient, then the actuators push against the anchoring points to provide a counterbalancing force.

Optionally, the actuators are configured automatically to move the support elements 14a, 14b, 14c between anchoring points on an intervention site $F_A$, $F_B$, $F_C$, $F_D$, without assistance so that the articulated robotic platform 10 can "walk" on the anchoring points around trajectory entry points under the control of a controller.

Optionally, the distal ends of the support elements 14a, 14b, 14c are provided with automatically lockable ends to enable engagement and disengagement from the anchor members. For example, servomotors on the distal ends of each support member are configured to operate a rotary detent that is engageable or disengageable with a support member.

The actuators may be provided as a servomechanism enabling each support member 14a, 14b, 14c, to perform three-dimensional (pitch and yaw) movement at the proximal ends of the support members attached to the base portion 12, and/or a rotary threaded (or rack and pinion) actuator causing telescoping support members 14a, 14b, 14c to lengthen or shorten. A skilled person will appreciate that many mechanical variations may be used to enable the support members 14a, 14b, 14c to lengthen, shorten, and to change orientation. The actuators are controlled by being configured to receive actuation data from a controller located on the articulated robotic platform 10, or via the articulated robotic arm 32. Accordingly, the articulated robotic platform 10 according to this embodiment can automatically and accurately follow the path 6 of an intervention.

A second aspect provides an articulated robotic arm 32 for medical tool positioning. The articulated robotic arm 32 comprises a plurality of articulated arm sections, wherein a distal articulated arm section of the plurality of articulated arm sections is supported by a base support. Furthermore, the articulated robot arm 32 comprises a proximal articulated arm section of the plurality of articulated arm sections comprising a second joint portion 33 configured to secure the proximal articulated arm section to an articulated robotic platform 10 according to the first aspect or its optional embodiments. The robotic arm is configured to apply a counterbalancing force to the articulated robotic platform to thus stabilise the articulated robotic platform. The articulated robotic arm 32 may be configured to communicate data signals to and from the articulated robotic platform 10 to a controller.

Figure 3:
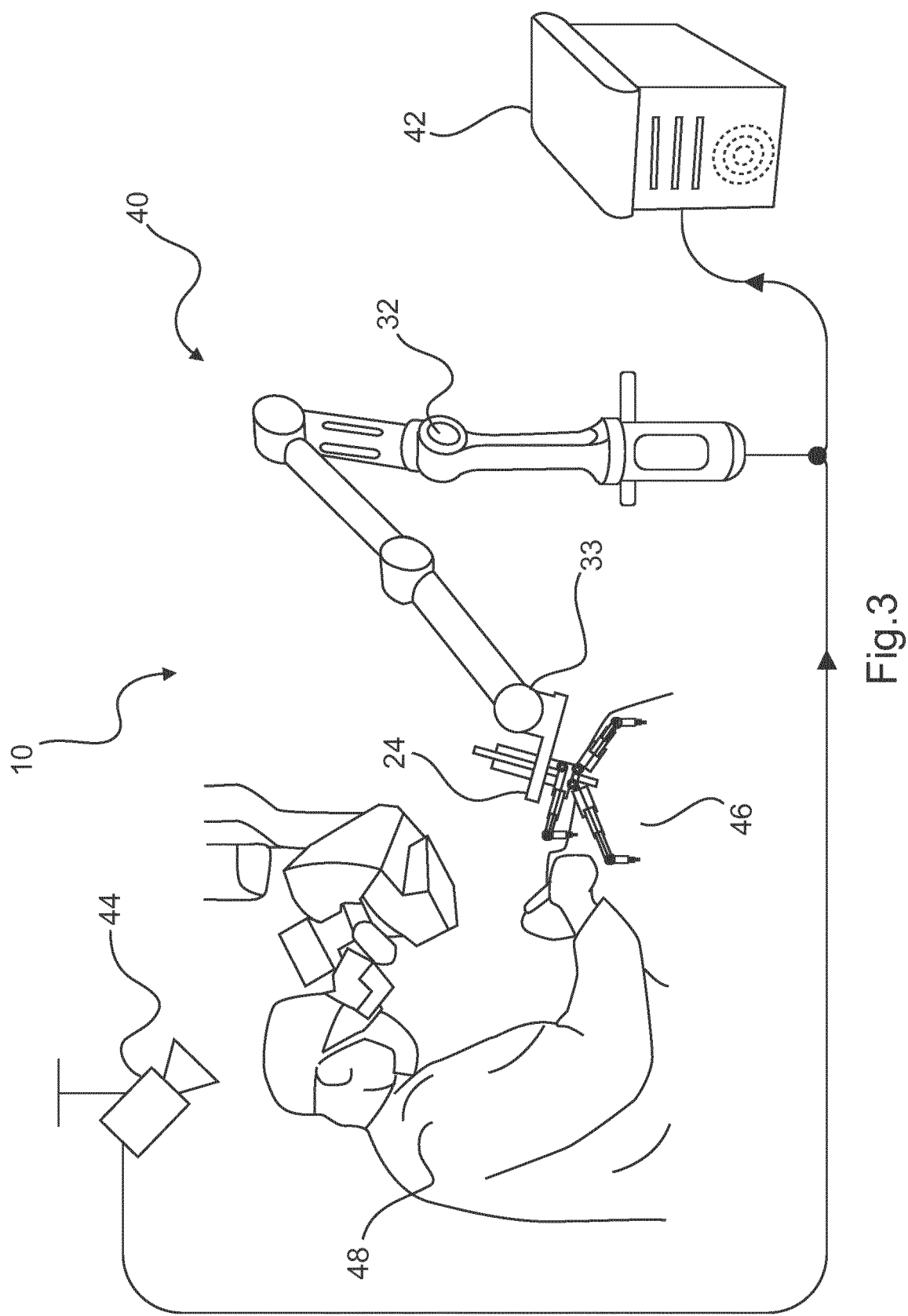
FIG. 3 schematically illustrates an example of a system for controlling the position of an articulated robotic platform in proximity to a patient.

FIG. 3 illustrates a schematic of a system in accordance with a third aspect.

FIG. 3 illustrates a medical professional performing an intervention on a patient's skull 46 using the system. The system 40 comprises a robotic arm 32 in accordance with the second aspect or its embodiments. The system 40 further comprises a articulated robotic platform 10 attached to a proximal end of the robotic arm 32 via a first joint portion 24 of the articulated robotic platform and a second joint portion 33 of the articulated robotic arm 32. The articulated robotic arm 32 is connected to a controller 42 which functions to provide position control data to position control motors in the articulated robotic arm 32 to enable repositioning of the proximal end of the articulated robotic arm 32. The controller 42 is configured to communicate with the articulated robotic platform 10 to receive, for example, extension measurement sensor data and/or force measurement data, and/or articulated joint orientation data from the support members 14a, 14b, 14c of the articulated robotic platform 10, and optionally to transmit actuator control data back to the articulated robotic platform 10 in the case of an "active" articulated robotic platform.

Optionally, the system 40 further comprises a imaging camera 44 (which may be a video camera, an infrared camera, et cetera) configured to capture the field of view containing the articulated robotic arm 32, the articulated robotic platform 10, and the region of intervention of the patient 46. Imaging data provided by the imaging camera 44 to the system 40 is optionally used to improve the registration of the articulated robotic arm 32 to the patient 46 and the articulated robotic platform 10.

In use, a medical professional attaches a passive or active articulated robotic platform to the second joint portion 33 at the proximal end of the articulated robotic arm 32. Prior to an interventional procedure, anchoring points are provided on a patient's skull according to a pre-prepared surgical plan. The patient geometry defined by the anchoring points is registered to the robot system geometry of the articulated robotic arm 32 and articulated robotic platform 10. Many techniques exist for generating this registration. As one example, the articulated robotic arm 32 having the articulated robotic platform 10 attached (passive or active case) can be moved close to a patient. Then, support member 14*a* of the articulated robotic platform 10 is guided (for example, by the medical professional) onto an anchor point. Because the anchor point has a known location relative to the patient geometry, and the support member 14*a* has a known location relative to the geometry of the articulated robotic arm 32, measurement data provided by measurement of the direction and/or extension of the support member 14*a* (from feedback of the extension measurement sensors of the articulated robotic platform) enables the two geometrical systems to be registered. Optionally or in addition, the imaging camera 44 captures the location of the anchoring points and the articulated robotic arm 32 and generates or updates the registration between the patient and the articulated robotic arm 32.

Once registered, a medical professional may position the articulated robotic platform 10 in a starting position (as illustrated in FIG. 2*a*)) and begin the intervention. The articulated robotic platform 10 may only need to be positioned in one position for the entire intervention in the case of a simple intervention, although the improved stabilisation resulting from the force counterbalance leads to improved accuracy. Alternatively, the articulated robotic platform may be moved between alternate trajectory entry points. In the case of a "passive" articulated robotic platform 10, a medical professional may detach the support members 14*a*, 14*b*, 14*c* and move them around. In the case of an "active" articulated robotic platform 10, actuators move the legs of the articulated robotic platform.

Optionally, controller 42 is connected to an output device (not shown). The output device may be configured to provide a range of feedback to a medical professional. For example, a graphical user interface (GUI) can provide a summary of the current and next stages of a medical plan. The GUI can be configured to display the orientation of the articulated robotic platform. The GUI can be configured to display an estimate of the current position accuracy of the articulated robotic platform. The GUI can be configured with an accuracy threshold, such that if the current position accuracy of the articulated robotic platform falls below the accuracy threshold, an alarm indicator is displayed.

Figure 4:
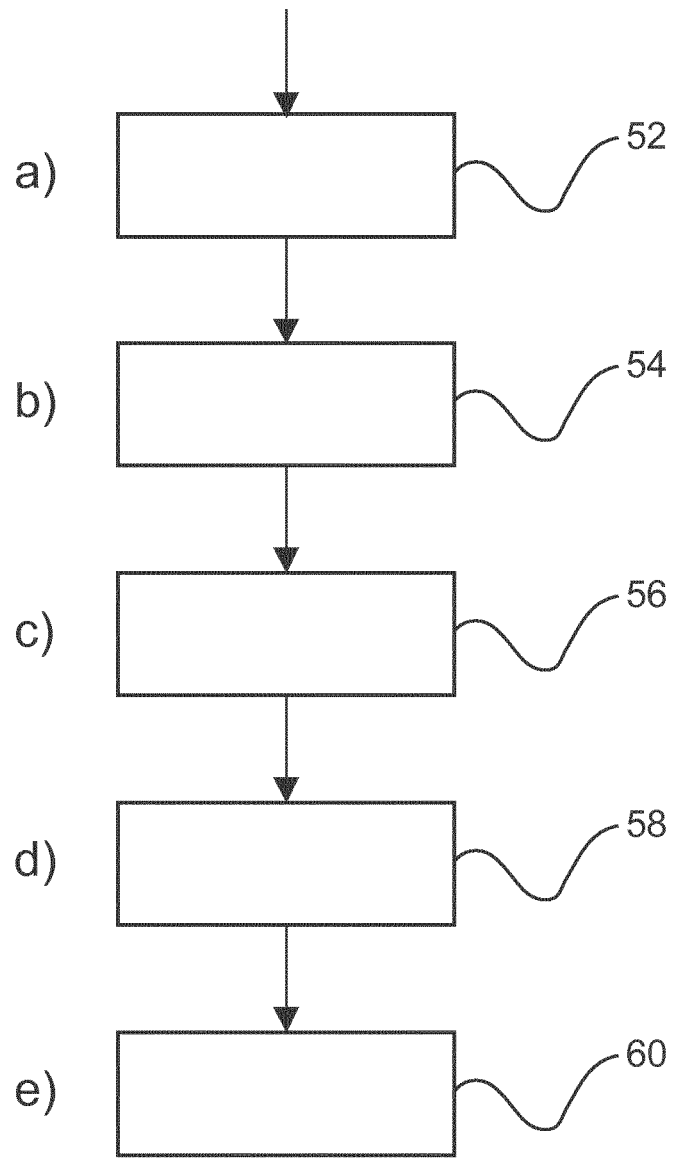
FIG. 4 schematically illustrates an example of a computer-implemented method for controlling the position of an articulated robotic platform.

FIG. 4 illustrates a computer-implemented method 50 according to a fourth aspect.

The computer-implemented method 50 for controlling the position of an articulated robotic platform according to the first aspect or its embodiments in proximity to a patient comprises:

a) acquiring 52 extension data from an extension measurement sensor of the articulated robotic platform;

b) acquiring 54 position data of an articulated robotic supporting the articulated robotic platform;

c) calculating 56 a first balancing force to be applied by the articulated robotic platform to the articulated robotic arm based on the position data of the articulated robotic arm and the extension data;

d) calculating 58 a second balancing force to be applied by the articulated robotic arm to the articulated robotic platform based on the position data of the articulated robotic arm and the extension data;

e) applying 60 the first and second balancing forces to the articulated robotic platform and the articulated robotic arm, respectively, such that the articulated robotic platform is held in a stable equilibrium in relation to the patient.

Optionally, in the case of a "passive" articulated robotic platform, the first balancing force is the equal and opposite reaction to a traction force applied as the second balancing force by the articulated robotic platform.

Optionally, the second balancing force is a traction force that pulls the articulated robotic platform away from a patient.

In use, the patient is prepared by placing bone fiducials. In the optional case of a crane intervention, bone fiducials are placed along a planned interventional path, with typically three bone fiducials positioned per interventional neighbourhood.

Preoperative scans are performed (for example, using CT), enabling the detection of the fiducials. The location of the articulated robotic arm 32 and the patient is typically known and fixed. Accordingly, the end-actuator (for example, a support arm 14*a* of the articulated robotic platform 10) of the articulated robotic arm may be brought into contact with the patient fiducials prior to the procedure to improve registration accuracy.

Subsequently, the articulated robotic arm 32 is brought into the correct area to follow a planned interventional path 6. The support members 14*a*, 14*b*, 14*c* of the articulated robotic platform are extended and fixed to the fiducial markers $F_A$, $F_B$, $F_C$ provided on the patient.

The mapping of the fiducial markers $F_A$, $F_B$, $F_C$ to the support members support members 14*a*, 14*b*, 14*c* can be derived by providing a camera-based detection, or by providing uniquely identifiable fiducials that can be detected by the support members 14*a*, 14*b*, 14*c* (because the exact location of the fiducials relative to the patient is known in advance). One exemplary way of providing uniquely identifiable fiducials discussed according to the first aspect is, for example, by providing each fiducial with an RFID tag, and providing each of the support members 14*a*, 14*b*, 14*c* with RFID reading means.

Optionally, the support members 14*a*, 14*b*, 14*c* can be shortened or lengthened through the application of tension using an actuator provided on the articulated robotic platform 10.

Accordingly, a stable and stiff connection can be achieved if the support members 14*a*, 14*b*, 14*c* are fixed to a skull and the articulated robotic arm 32 pulls away from the articulated robotic platform 10 with an equal force. Accordingly, the articulated robotic platform 10 navigates itself to optimally fit the planned path 6.

When the first stage of the medical procedure is completed, one or more of the support members 14*a*, 14*b*, 14*c* are released and the robot can be repositioned by a medical professional onto a new combination of fiducial markers.

Further examples will now be provided assuming that the preconditions (i) that the fiducial locations in 3D space in relation to a patient are known (for example, via a preoperative scan), and that (ii) at least one interventional trajectory has been planned, and thus has a known coordinate and route in 3D space.

Several variations of the articulated robotic platform according to the first aspect may be envisaged, and these may be considered in terms of boundary conditions. For example:

(1) An articulated robotic arm 32 with exact positioning abilities can be provided (in other words, with an actuator capable of positioning the articulated robotic platform 10 to millimetre or sub-millimetre accuracy), or an articulated robotic arm 32 with inexact positioning abilities is provided (in other words, the articulated robotic platform 10 may not be capable of attaining millimetre or sub-millimetre accuracy because the articulated robotic arm 32 to which it is attached is inexact).

(2) An articulated robotic platform 10 may be provided with support members 14 capable of actuated movement (as in the "active" case described above), or alternatively an articulated robotic platform 10 may be provided with support members 14 that can only be stiffened by traction from an externally connected articulated robotic arm 32 (as in the "passive" case described above).

(3) An articulated robotic platform 10 can be provided with three articulated support members 14, or any other number of support members 14.

(4) Articulated robotic platform 10 can be provided with support members 14 capable of sensing the identity of fiducials, versus an articulated robotic platform 10 with support members 14 that cannot sense the identity of fiducials.

According to a one case, it is assumed that an articulated robotic arm 32 having inexact positioning abilities is provided, with an articulated robotic platform 10 having support members that can be stiffened by traction from the articulated robotic arm 32 only. The support members, and/or the articulated robotic platform comprise force sensors, such as an extension measurement sensor connected to each support member. In this example, an articulated robotic platform 10 having three support members 14a, 14b, 14c wherein the fiducials cannot automatically be detected by the three support members 14a, 14b, 14c. This may be thought of as a low-cost, passive example of the articulated robotic platform 10.

The necessary data processing to support this version of an articulated robotic platform 10 comprises calculating the target position of the medical tool support 18 based on the known geometry of the medical tool support 18 and the planned interventional trajectory (pre-calculated information), in such a way that the tool will be inserted into a skull along the planned trajectory as registered to a patient.

Then, a data processing step calculates the target extension of the support members 14a, 14b, 14c of the articulated robotic platform 10 to enable the medical tool support 18 to be positioned at its target position. The data processing step also calculates which of the support members 14a, 14b, 14c should be calculated to which of the fiducials $F_A$, $F_B$, $F_C$.

The result of this data processing step is output to a user (such as a medical professional) using the articulated robotic platform 10 in the system.

The robot is moved into a position enabling the support members 14a, 14b, 14c of the articulated robotic platform 10 to be attached to the calculated fiducials $F_A$, $F_B$, $F_C$. The user then attaches the legs to the fiducials.

Then, a robot-arm based positioning phase, when a low-resolution positioning of the articulated robotic platform is undertaken. In this phase, the measured extension of each of the support members 14a, 14b, 14c is used to calculate the current position of the medical tool support 18. An updated position, and the required movement demand signal to the articulated robot arm 32 necessary to effect this movement is calculated.

The articulated robotic arm 32 is then moved to the newly completed position. This step is optionally iterated several times until a low-resolution positioning criterion is met. For example, the low-resolution positioning criterion can position the articulated robotic platform to within a couple of millimetres of accuracy relative to the trajectory entry point.

A subsequent step is a counter-force positioning phase in which higher-resolution positioning than the robot-arm based positioning phase is possible thanks to the counter-force and/or extension feedback data from the articulated robotic platform 10. This phase is optionally considered as a background phase that is ongoing during the whole surgical procedure because the actual position of the articulated robotic platform 10 must be evaluated, reported and possibly corrected at any time in response to an additional external force applied by a surgeon when moving surgical tool in the medical tool support 18, for example. For example, the high-resolution positioning criterion can position the articulated robotic platform to within sub-millimetre accuracy relative to the trajectory entry point.

The high-resolution positioning phase comprises calculating the current position of the medical tool support 18 based upon the measured extent of the support members 14a, 14b, 14c.

The current force vectors of the legs are measured, for example by force sensors attached to the support members 14a, 14b, 14c, and the current force vector of the articulated robot arm 32 is measured. Force sensor data of the support members 14a, 14b, 14c and a current force vector of the articulated robot arm 32 is collected and provided to a controller.

The deviation of the medical tool support 18 to the exact target position is calculated by the controller based on the current position of the medical tool support 18, and the current force vectors.

Update force vectors are determined by the controller for the support members 14a, 14b, 14c and the articulated robotic arm 32, and these forces are applied to the articulated robotic platform 10 by updating the vector of the traction force provided by the articulated robotic arm 32 causing the position of the articulated robotic platform 10 to change to a new equilibrium position, and with it the position of the medical tool support 18. The derivation of the updated force vectors may be calculated, for example, via a lookup table created previously based on a hardware specific evaluation of the forces versus the position mapping, or using a control-theory approach in which an incremental position change caused by a small incremental change in the applied force vector is used to position the articulated robotic platform 10 accurately.

Optionally, an output provided to a user on a display screen of the system reports to user if the precision of the position accuracy is presently sufficient for the interventional procedure to proceed.

According to a more complicated case of a articulated robotic platform 10 within the boundary conditions discussed above, it is assumed that a sophisticated articulated robotic platform having exact (in other words, millimetre or sub-millimetre accuracy) is provided. The articulated robotic platform 10 is provided with actuated (self-moving) support members 14*a*, 14*b*, 14*c*. It is assumed that the articulated robot has three self-movable articulated legs and the support members have detectors (for example, RFID detectors) that can automatically detect unique placed fiducials on the patient according to the producer placement plan.

In this case, it is necessary to calculate a target extent of each of the support members 14*a*, 14*b*, 14*c* of the articulated robotic platform 10 in such a way that the medical tool support 18 will be positioned at its target position as defined by the trajectory planning software step. The software also defines which support member 14*a*, 14*b*, 14*c* should be attached to a particular fiducial $F_A$, $F_B$, $F_C$.

There follows an iterative robot-arm based positioning phase, where the current position of the medical tool support 18 is calculated using the precisely detected position of the articulated robotic arm 32 and the measured extent of the support members 14*a*, 14*b*, 14*c* giving more confidence about the exact position of the medical tool support 18. Actuators of the articulated robotic platform 10 and the articulated robotic arm 32 are controlled to move the articulated robotic platform to a position in proximity to the patient where the support members 14*a*, 14*b*, 14*c* can be attached to the fiducials $F_A$, $F_B$, $F_C$. Subsequently, the support members 14*a*, 14*b*, 14*c* attach themselves to the correct and preplanned fiducials $F_A$, $F_B$, $F_C$. For example, the low-resolution positioning criterion can position the articulated robotic platform to within a millimetre of accuracy relative to the trajectory entry point.

Subsequently, an iterative counter-force based (high-resolution) positioning phase operative during the medical intervention evaluates the actual position of the medical tool support 18 based on the precisely detected articulated robotic arm position and the measured extent of the support members 14*a*, 14*b*, 14*c* providing enhanced confidence about the exact position of the medical tool support 18 (to within millimetre or sub-millimetre accuracy). For example, the high-resolution positioning criterion can position the articulated robotic platform to within sub-millimetre accuracy relative to the trajectory entry point.

In this case, the counter-force provided by the articulated robotic platform may be either a pushing force or a pulling force towards, or away from, the articulated robotic arm.

The invention claimed is:

1. An articulated robotic platform for medical tool positioning, comprising:
   a medical tool support;
   a plurality of support members connected to the medical tool support, wherein at least one support member comprises an articulated connection to the medical tool support and a distal end configured to be directly attached to an anchor member provided as a fiducial marker; and
   a first joint portion configured to secure the articulated robotic platform in a controlled spatial relationship to an articulated robotic arm,
   wherein the articulated robotic platform further comprises at least one positioning sensor configured for determining a position of the articulated robotic platform, wherein the at least one positioning sensor is at least partly disposed at the at least one support member,
   wherein the articulated robotic platform is configured to move along an intervention path defined by a plurality of independent anchor members by repositioning the at least one support member at a next anchor member along the intervention path, the next anchor member provided as a next fiducial marker, by directly attaching the distal end of the at least one support member to the next fiducial marker.

2. The articulated robotic platform according to claim 1, wherein the at least one positioning sensor further comprises an optical navigation sensor and/or an x-ray navigation sensor.

3. The articulated robotic platform according to claim 1, wherein the at least one positioning sensor further comprises:
   at least one extension measurement sensor configured to measure an extension of the at least one support member; and/or
   at least one angle sensor configured for measuring an angle between the at least one support member and the medical tool support.

4. The articulated robotic platform according to claim 3, wherein the at least one extension measurement sensor comprises a tensionable cord fixed to a distal portion of the at least one support member and a cord tensioning reel comprised in a proximal portion of the at least one support member and/or the medical tool support.

5. The articulated robotic platform according to claim 1, wherein the at least one support member comprises an anchor member sensor configured to identify between at least first and second different types of fiducial markers.

6. The articulated robotic platform according to claim 1, wherein one or more of: the articulated robotic platform, a portion of the at least one support member, and/or the first joint portion comprise a radiopaque material.

7. The articulated robotic platform according to claim 1, further comprising:
   a support hub,
   wherein the medical tool support, the plurality of support members, and the first joint portion are attached to the support hub.

8. The articulated robotic platform according to claim 1, further comprising:
   an actuator configured to move the at least one support member.

9. The articulated robotic platform according to claim 1, wherein the articulated robotic arm comprises:
   a plurality of articulated arm sections, wherein a distal articulated arm section of the plurality of articulated arm sections is supported by a base support, wherein a proximal articulated arm section of the plurality of articulated arm sections comprises a second joint portion configured to secure the proximal articulated arm section to the articulated robotic platform,
   wherein the articulated robotic arm is configured to apply a counterbalancing force against a balancing force of the articulated robotic platform to thus stabilize the articulated robotic platform.

10. The articulated robotic platform according to claim 9, further comprising:
   a force sensor configured to measure force applied to the articulated robotic platform at the first joint portion; and
   a processor configured to:
      receive positioning data from the at least one positioning sensor;
      calculate a required force demand to be applied by the articulated robotic arm; and
      communicate the required force demand to the articulated robotic arm via the first joint portion to enable the articulated robotic platform to be held in a stable equilibrium.

11. The articulated robotic platform according to claim 1, wherein parts of the at least one positioning sensor are disposed at the medical tool support and parts of the at least one positioning sensor are disposed at the distal end of the at least one support member.

12. The articulated robotic platform according to claim 1, wherein the articulated robotic platform is made of a disposable material and is disposable and/or the articulated robotic platform is made of a lightweight material and a total weight of the articulated robotic platform is in a range of 25 grams to 250 grams.

13. The articulated robotic platform according to claim 1, wherein the distal end of the at least one support member has a lockable end adapted to enable engagement with and disengagement from the anchor member.

14. A system for controlling a position of an articulated robotic platform in proximity to a patient, the system comprising:
an articulated robotic arm including a plurality of articulated arm sections, wherein a distal articulated arm section of the plurality of articulated arm sections is supported by a base support, wherein a proximal articulated arm section of the plurality of articulated arm sections comprises a second joint portion; and
the articulated robotic platform comprising:
a medical tool support;
a plurality of support members connected to the medical tool support, wherein at least one support member comprises an articulated connection to the medical tool support and a distal end configured to be directly attached to an anchor member provided as a fiducial marker;
a first joint portion configured to secure the articulated robotic platform in a controlled spatial relationship to the articulated robotic arm; and
at least one positioning sensor configured for determining a position of the articulated robotic platform, wherein the at least one positioning sensor is at least partly disposed at the at least one support member,
wherein the first joint portion of the articulated robotic platform is connected to the second joint portion of the articulated robotic arm to enable the articulated robotic platform to balance against a counterbalancing force provided, in operation, by the articulated robotic arm to stabilize the articulated robotic platform,
wherein the articulated robotic platform is configured to move along an intervention path defined by a plurality of independent anchor members by repositioning the at least one support member at a next anchor member along the intervention path, the next anchor member provided as a next fiducial marker, by directly attaching the distal end of the at least one support member to the next fiducial marker.

15. The system according to claim 14, further comprising:
a controller,
wherein the controller is configured to:
acquire position configuration data of the articulated robotic arm, position configuration data of the articulated robotic platform, and registration data of registration between the articulated robotic arm and the articulated robotic platform; and
generate control data for at least one of the plurality of support members, the articulated robotic arm, and the second joint portion of the articulated robotic arm and/or the first joint portion of the articulated robotic platform based on the position configuration data of the articulated robotic arm, the position configuration data of the articulated robotic platform, and the registration data,
wherein the generated control data is calculated to (i) cause the articulated robotic platform to be held in a stable equilibrium against a counterforce provided by the articulated robotic arm; or (ii) to cause the articulated robotic platform to move relative to an anchor member to which the articulated robotic platform is attached.

16. The system according to claim 15, further comprising:
at least one image sensor or video sensor arranged to obtain an image or a video of a region of interest, the articulated robotic arm, and the articulated robotic platform,
wherein the at least one image sensor or video sensor is configured to acquire an image and/or a video of an anchor member, the articulated robotic platform, and the articulated robotic arm in the region of interest, and
wherein the controller is configured to generate a mapping of the anchor member to the at least one support member of the articulated robotic platform using the image and/or the video acquired from the at least one image sensor or video sensor.

17. The system according to claim 15, wherein the controller is further configured to:
instruct the articulated robotic arm to cooperate and move with the articulated robotic platform as the articulated robotic platform is moved to a new position.

18. The system according to claim 15, wherein the distal end of the at least one support member comprises an anchor member sensor such that the distal end is adapted to:
detect an identity of the anchor member the distal end is attached to or is set to be attached to; and
transmit information about the identity of the anchor member to the controller via the first joint portion or a wireless connection.

* * * * *

UNITED STATES PATENT AND TRADEMARK OFFICE
CERTIFICATE OF CORRECTION

| | | |
|---|---|---|
| PATENT NO. | : 12,257,009 B2 | Page 1 of 1 |
| APPLICATION NO. | : 17/256713 | |
| DATED | : March 25, 2025 | |
| INVENTOR(S) | : Bálint Várkuti and Dirk Schöttle | |

It is certified that error appears in the above-identified patent and that said Letters Patent is hereby corrected as shown below:

On the Title Page

Item (12) should read as --Várkuti et al.-- and
Item (72) the first inventor's name should read as --Bálint Várkuti--.

Signed and Sealed this
Twentieth Day of May, 2025

Coke Morgan Stewart
*Acting Director of the United States Patent and Trademark Office*